US007070944B2

(12) United States Patent
Black et al.

(10) Patent No.: US 7,070,944 B2
(45) Date of Patent: Jul. 4, 2006

(54) SYSTEM FOR SCREENING FATTY ACID TRANSPORT INHIBITORS, METHODS OF USE AND MODULATORS IDENTIFIED THEREBY

(75) Inventors: Paul Black, Slingerlands, NY (US); Concetta DiRusso, Slingerlands, NY (US)

(73) Assignee: CLF Medical Technology Acceleration Program, Inc., Clifton, Park, NY (US)

( * ) Notice: Subject to any disclaimer, the term of this patent is extended or adjusted under 35 U.S.C. 154(b) by 393 days.

(21) Appl. No.: 10/099,350

(22) Filed: Mar. 14, 2002

(65) Prior Publication Data

US 2002/0182197 A1    Dec. 5, 2002

Related U.S. Application Data

(60) Provisional application No. 60/304,869, filed on Jul. 12, 2001, provisional application No. 60/304,850, filed on Jul. 12, 2001, provisional application No. 60/296,861, filed on Jun. 8, 2001, provisional application No. 60/275,726, filed on Mar. 14, 2001.

(51) Int. Cl.
*G01N 33/53*    (2006.01)
*C12N 1/20*    (2006.01)

(52) U.S. Cl. ............... 435/7.21; 435/252.3; 435/252.8; 435/325; 435/69.1; 435/7.1; 435/7.2; 435/7.37; 435/71.1; 435/71.2; 435/350

(58) Field of Classification Search ............... 435/7.21, 435/252.3, 252.8, 325, 69.1, 7.1, 7.2, 7.37, 435/71.1, 71.2; 530/350
See application file for complete search history.

(56) References Cited

U.S. PATENT DOCUMENTS

| | | | |
|---|---|---|---|
| 6,284,487 B1 | 9/2001 | Stahl et al. | 435/69.1 |
| 6,288,213 B1 | 9/2001 | Stahl et al. | 530/350 |
| 6,300,096 B1 | 10/2001 | Stahl et al. | 435/69.1 |
| 6,348,321 B1 | 2/2002 | Stahl et al. | 435/7.21 |
| 6,657,049 B1 | 12/2003 | Stahl | 530/387.9 |
| 2002/0106733 A1 | 8/2002 | Stahl et al. | 435/69.1 |
| 2003/0232363 A1 | 12/2003 | Stahl et al. | 435/6 |

OTHER PUBLICATIONS

Knoll et al. Biochemical Studies of Three *Saccharomyces cerevisiae* Acyl-CoA Synthetase, Faa1p, Faa2p, Faa3p. The Journal of Biological Chemistry. vol. 269, No. 23, pp. 16348-16356, 1994.*
Raman, et al. (1997). "Characterization of the Fatty Acid-responsive Transcription Factor FadR." *J. Biol. Chem.*, 272: 30645.
Faergman, et al. (1997). "Disruption of the *Saccharomyces cerevisiae* Homologue to the Murine Fatty Acid Transport Protein Impairs Uptake and Growth on Long-chain Fatty Acids." *J. Biol. Chem.*, 272: 8531.
DiRusso, et al. (2000). "Murine FATP alleviates growth and biochemical deficiencies of yeast *fat1* Δ strains." *Eur. J. Biochem.*, 267: 1-13.
Black, et al. (2000). "Long Chain Acyl-CoA-Dependent Regulation of Gene Expression in Bacteria, Yeast and Mammals." *Symposium: The Role of Long Chain Fatty Acyl-CoAs as Signaling Molecules in Cellular Metabolism, Amer. Soc. Nutritional Sciences*, 305S.
Faergman, et al. (2001). "The Acyl-CoA Synthetase Encoded within FAA1 FAA4 in *Saccharomyces cerevisiae* Function as Components of the Fatty Acid Transport System Linking Import, Activation, and Intracellular Utilization." *J. Biol. Chem.* 276: 37051.

* cited by examiner

*Primary Examiner*—Eileen B. O'Hara
*Assistant Examiner*—Fozia Hamud
(74) *Attorney, Agent, or Firm*—Ivor R. Elrifi, Esq.; Naomi S. Biswas, Esq.; Mintz, Levin, Cohn,Ferris, Glovsky and Popeo, P.C.

(57) ABSTRACT

Methods for identifying modulators of fatty acid transport and/or uptake, comprising contacting, under conditions favorable for fatty acid uptake, a putative modulator, e.g., an inhibitor with a system comprising genetic material encoding a fatty acid transport mediator ("TTM"), particularly FAA1, FAA2, FAA3, FAA4, FAT1, fadL, fadD, FATP, CD36 and FABP, or orthologs, homologs, isoforms, variants, analogs, derivatives or fragments thereof, and combinations thereof, or fatty acid transport mediator proteins ("TTMps"), e.g., Faa1p, Faa2p, Faa3p, Faa4p, Fat1p, FadL, fatty acyl CoA synthetase, FATP, CD36 and FABP, or orthologs, homologs, isoforms, variants, analogs, derivatives or fragments thereof, and combinations thereof, and determining the effect of the putative modulator. The test system may be a cell such as *Saccharomyces cerevisiae, E. coli, H. sapiens,* etc. or an in vitro system.

18 Claims, 14 Drawing Sheets

A. YPD

B. YPD-CER

C. YPD-CER-OLE

A. YNBD-EG

B. YNBD-EG-OLE

A. Fat1p-GFP in W303a yeast    B. GFP imaging of Panel A yeast

SYSTEM FOR SCREENING FATTY ACID TRANSPORT INHIBITORS, METHODS OF USE AND MODULATORS IDENTIFIED THEREBY

RELATED APPLICATIONS

This application claims the benefit of priority under 35 U.S.C. §119(e) to copending U.S. Provisional Application Nos. 60/275,726, filed on Mar. 14, 2001; 60/296,861, filed on Jun. 8, 2001; 60/304,850, filed on Jul. 12, 2001; 60/304,869, filed on Jul. 12, 2001; the entire contents of which are incorporated herein by reference.

STATEMENT AS TO FEDERALLY SPONSORED RESEARCH

This invention was made with partial U.S. Government support under National Institutes of Health grant GM56840. The government has certain rights in the invention.

BACKGROUND OF THE INVENTION

Long chain fatty acids (LCFAs) are an important source of (energy for most organisms. They also function as blood hormones, regulating key metabolic functions such as hepatic glucose production. Although LCFAs can diffuse through the hydrophobic core of the plasma membrane into cells, this nonspecific transport cannot account for the high affinity and specific transport of LCFAs exhibited by cells such as cardiac muscle, hepatocytes, enterocytes, and adipocytes. The molecular mechanisms of LCFA transport remains largely unknown. Identifying these mechanisms can lead to pharmaceuticals that modulate fatty acid uptake by the intestine and by other organs, thereby alleviating certain medical conditions (e.g. obesity, diabetes, hypotension or cardiomyopathy).

SUMMARY OF THE INVENTION

The invention provides methods for identifying modulators of fatty acid transport and/or uptake, comprising contacting, under conditions favorable for fatty acid uptake, a putative modulator, e.g., an inhibitor with a system comprising genetic material encoding a mediator of fatty acid transport mediator ("TTM"), particularly FAA1, FAA2, FAA3, FAA4, FAT1, FATP, CD36, and FABP, or orthologs thereof (e.g., rat, mouse, or human orthologs), or isoforms, homologs, analogs, variants, derivatives, or fragments thereof, and determining the effect of the putative modulator on fatty acid uptake or transport. The test system may be a eukaryotic cell such as Saccharomyces cerevisiae, or a prokaryotic cell such as E. coli, or an in vitro system, that has been provided with at least one exogenous gene encoding a TTM of the invention. In a preferred embodiment, the endogenous gene for the TTM is nonfunctional, and an exogenous orthologous TTM is provided. In a specific embodiment, the ortholog TTM is mammalian, including, e.g., mouse, rat, or human.

The invention further provides a cell whose endogenous genes encoding a TTM are nonfunctional, for instance, due to mutation, alteration or deletion of said endogenous gene. The cell may be a eukaryotic cell such as Saccharomyces cerevisiae, or a prokaryotic cell such as Escherichia coli. In a specific embodiment, the cell is a yeast cell of the genotype fat1Δ. In another embodiment, the cell is a yeast cell of the genotype faa1Δ, fat1Δ. In a further embodiment, the cell is a yeast cell of the genotype faa1Δ, faa4Δ, fat1Δ. In additional embodiments, the cell is a yeast cell of the genotype faa4Δ, fat1Δ or the genotype faa1Δ, faa4Δ. In an alternate embodiment, the cell is an E. coli cell whose genes for FadL (fadL) and fatty acyl CoA synthetase (fadD) are nonfunctional.

The invention further relates to modulators identified by the methods of the invention, which may inhibit fatty acid uptake or vectoral acylation of a TTMp, e.g., at least one of FAA1, FAA2, FAA3, FAA4, FAT1, FATP, CD36, and FABP, or orthologs, homologs, isoforms, variants, analogs, derivatives and fragments thereof. In certain embodiments, the TTMp consists of a pair of proteins, namely a membrane-associated TTMp and a cytosol-associated TTMp. In a specific embodiment, the TTMp pair is FAA1 and FAT1. In another embodiment, the TTMp pair is FAA4 and FAT1. In a further embodiment, the TTMp pair is FAA1 and FAA4. In yet another embodiment, the TTMp pair is CD36 and FABP. In an alternative embodiment, the TTMp pair is FadL and fatty acyl CoA synthetase. In an additional embodiment, three TTMps are provided, namely Faa1p, Faa4p and Fat1p.

The invention further relates to methods of weight reduction and/or weight management, comprising administering to a subject in which weight reduction and/or weight management is desired, an effective amount of a fatty acid uptake inhibitor, such as those identified by the methods of the invention, such that fatty acid uptake is reduced or that weight management is achieved.

The invention even further relates to methods of weight reduction and/or weight management, comprising administering to a subject in which weight reduction and/or weight management is desired, an effective amount of a TTM or TTMp inhibitor, such as those identified by the methods of the invention, such that fatty acid uptake is reduced or that weight management is achieved.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

("3") and pRS316 (vector control) ("4") on YPD (FIG. 2A), YPD supplemented with cerulenin (YPD-CER) (FIG. 2B) and YPD supplemented with cerulenin and oleate (YPD-CER-OLE) (FIG. 2C).

FIGS. 3A and 3B. Fat1p or FATP is required for growth of yeast under oxygen limiting conditions. Wild-type ("1") and fat1Δ strains transformed with pDB104 (murine-FATP) ("2"), pDB102 (yeast-FAT1) ("3") and pRS316 (vector control) ("4") were grown on YNBD supplemented with ergosterol (YNBD-EG) (FIG. 3A) or YNBD supplemented with ergosterol and oleate (YNBD-EG-OLE) (FIG. 3B) as shown.

Figure 4:
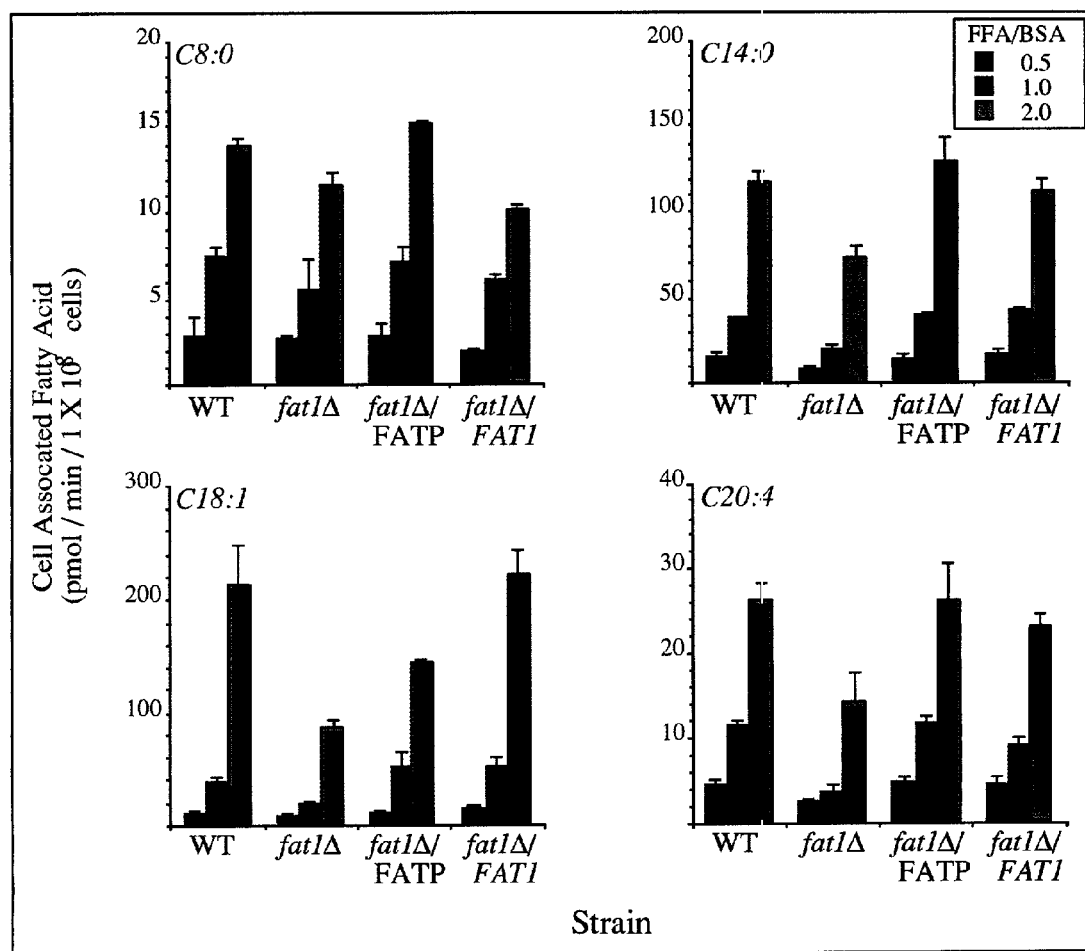

FIGS. 4A, 4B, 4C and 4D. Import of radioactively labelled fatty acids requires Fat1p or FATP. Fatty acid transport in wild-type, fat1Δ and fat1Δ strains transformed with pDB104 (FATP) or pDB102 (FAT1) was measured using three different FFA/BSA ratios. The error bars represent the standard error of the mean from four independent experiments. Specific fatty acids tested were C8:0 (FIG. 4A), C14:0 (FIG. 4B), C18:1 (FIG. 4C) and C20:4 (FIG. 4D).

Figure 5:
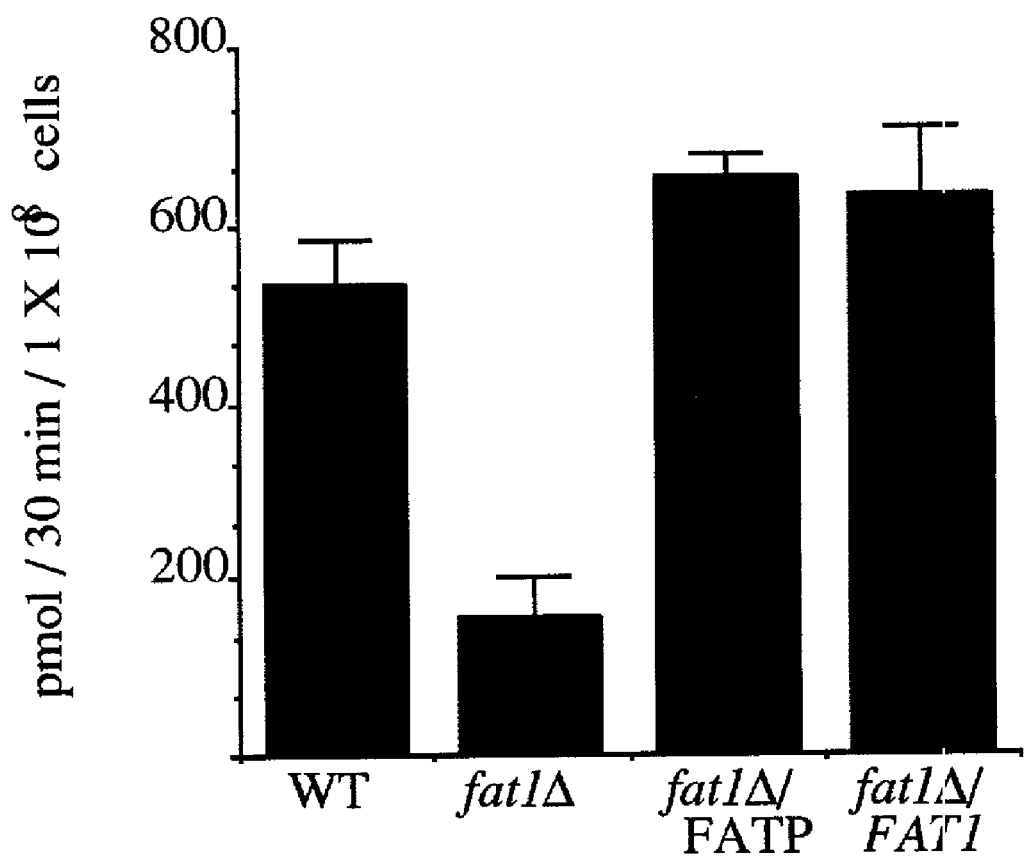

FIG. 5. In vivo β-oxidation is depressed in fat1Δ strains and restored by cloned Fat1p or FATP. β-oxidation of C18:1 was measured in wild-type, fat1Δ and fat1Δ strains transformed with pDB104 (murine FATP) or pDB102 (yeast FAT1) after growth in media containing oleate to induce peroxisomal proliferation. The error bars represent the standard error of the mean from three independent experiments.

Figure 6:
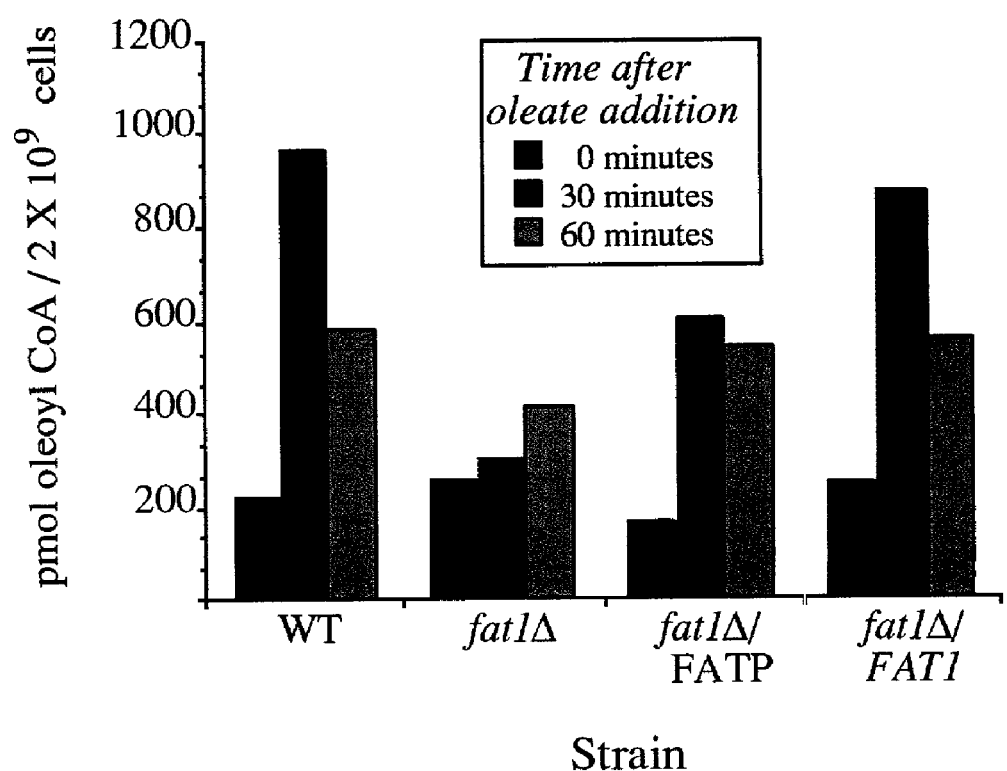

FIG. 6. Elevation of intracellular oleoyl-CoA level occurs as a result of Fat1p-dependent oleate import. Oleoyl-CoA levels were measured at the times indicated after the addition of 100 μM oleate to growth media in wild-type, fat1Δ and fat1Δ strains transformed with pDB104 (FATP) or pDB102 (FAT 1).

Figure 7:
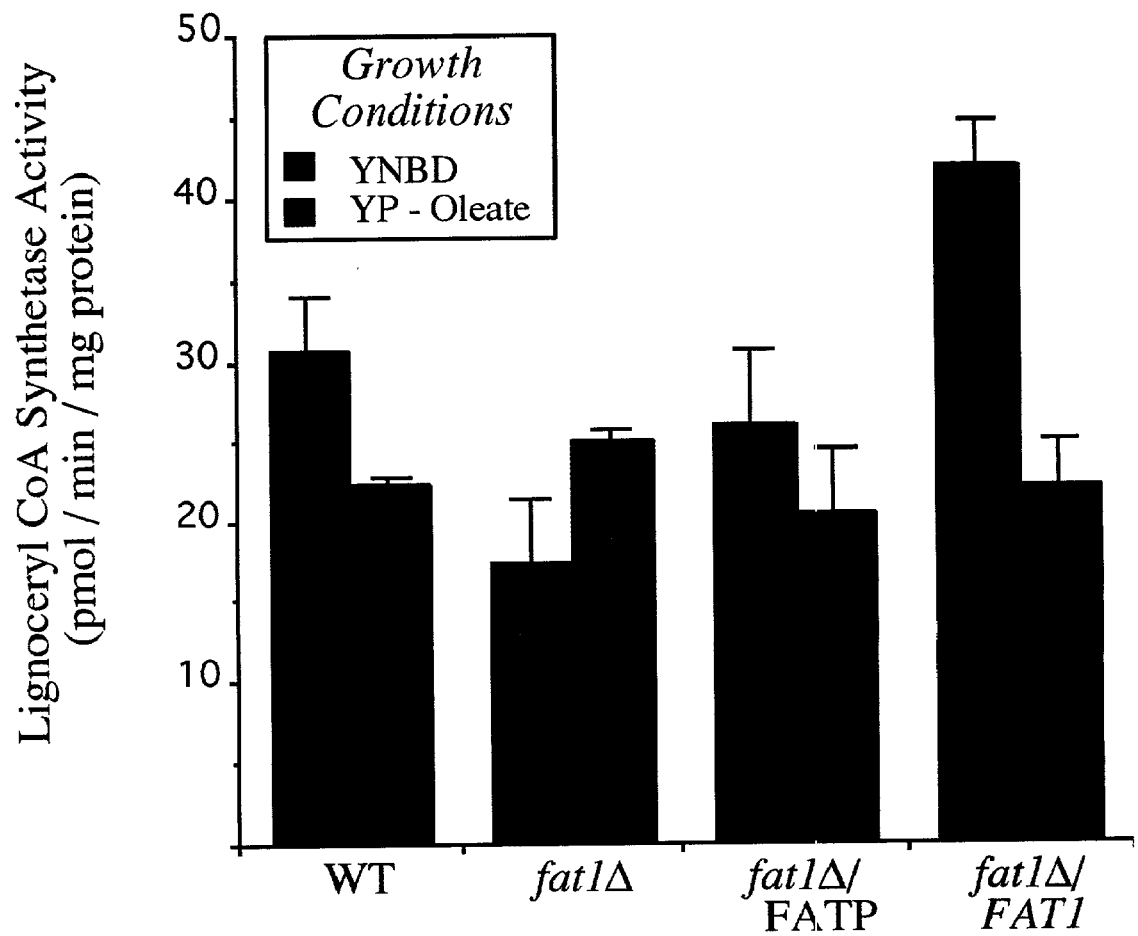

FIG. 7. Lignoceryl-CoA synthetase activities are partially dependent on Fat1p. Lignoceryl-CoA synthetase activities were measured in extracts of wild-type, fat1Δ and fat1Δ strains transformed with pDB104 (FATP) or pDB102 (FAT1) following growth in YNBD or YP-oleate.

Figure 8:
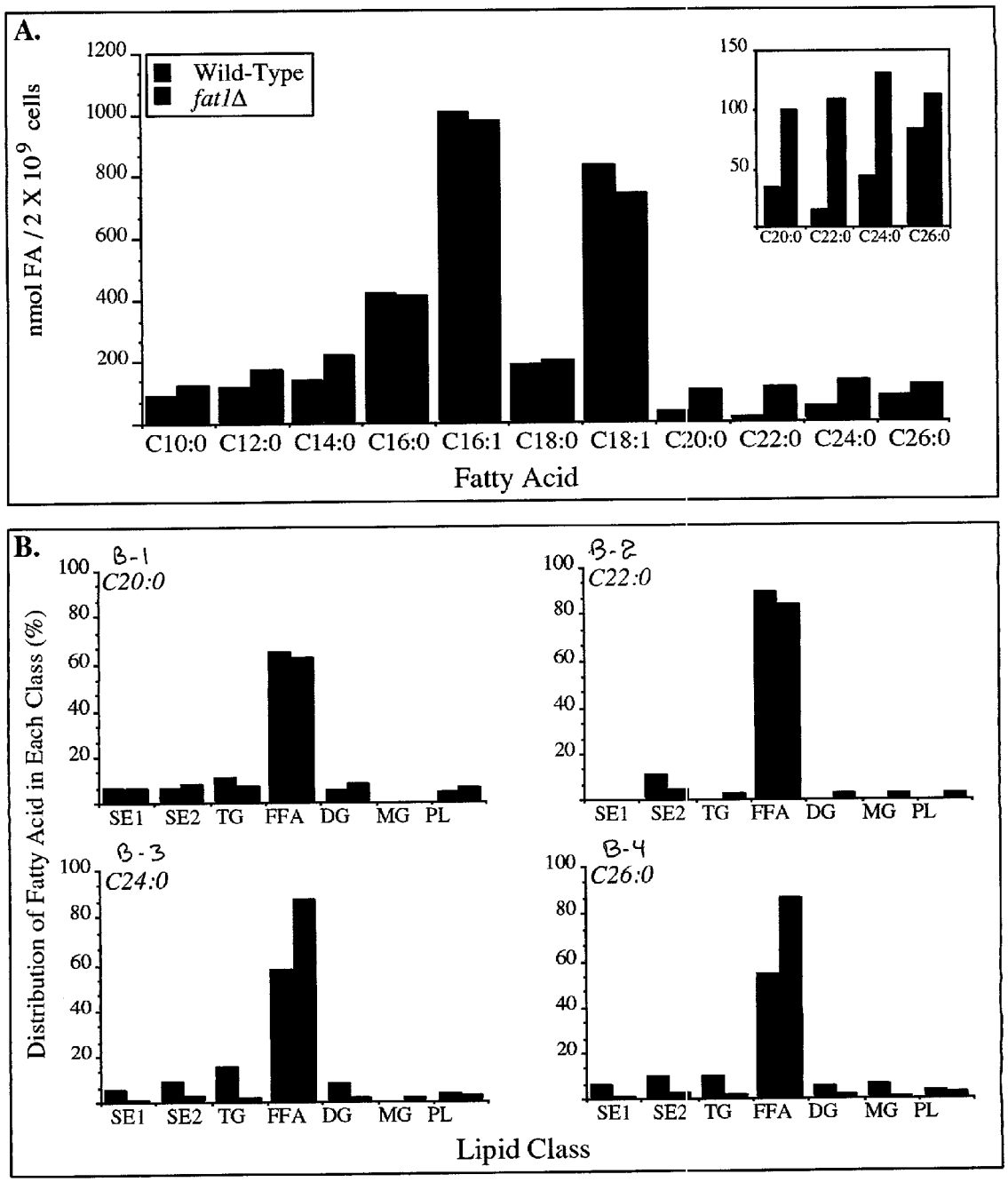

FIGS. 8A and 8B. Elevation of free very long chain fatty acid pools occurs when FAT1 is deleted. Lipid analyses were performed as detailed in the text. FIG. 8A shows total fatty acid composition in wild-type and fat1Δ strains; insert expands the data for C20:0, C22:0, C24:0 and C26:0 fatty acids. The four panels of FIG. 8B shows percent distribution of C20:0 (FIG. 8B-1), C22:0 (FIG. 8B-2), C24:0 (FIG. 8B-3) and C26:0 (FIG. 8B-4) in the various lipid classes. SE1 and SE2—steroyl esters; TG—triglycerides; FFA—free fatty acids; DG—diglycerides, MG—monoglycerides; and PL—total phospholipid.

Figure 9:
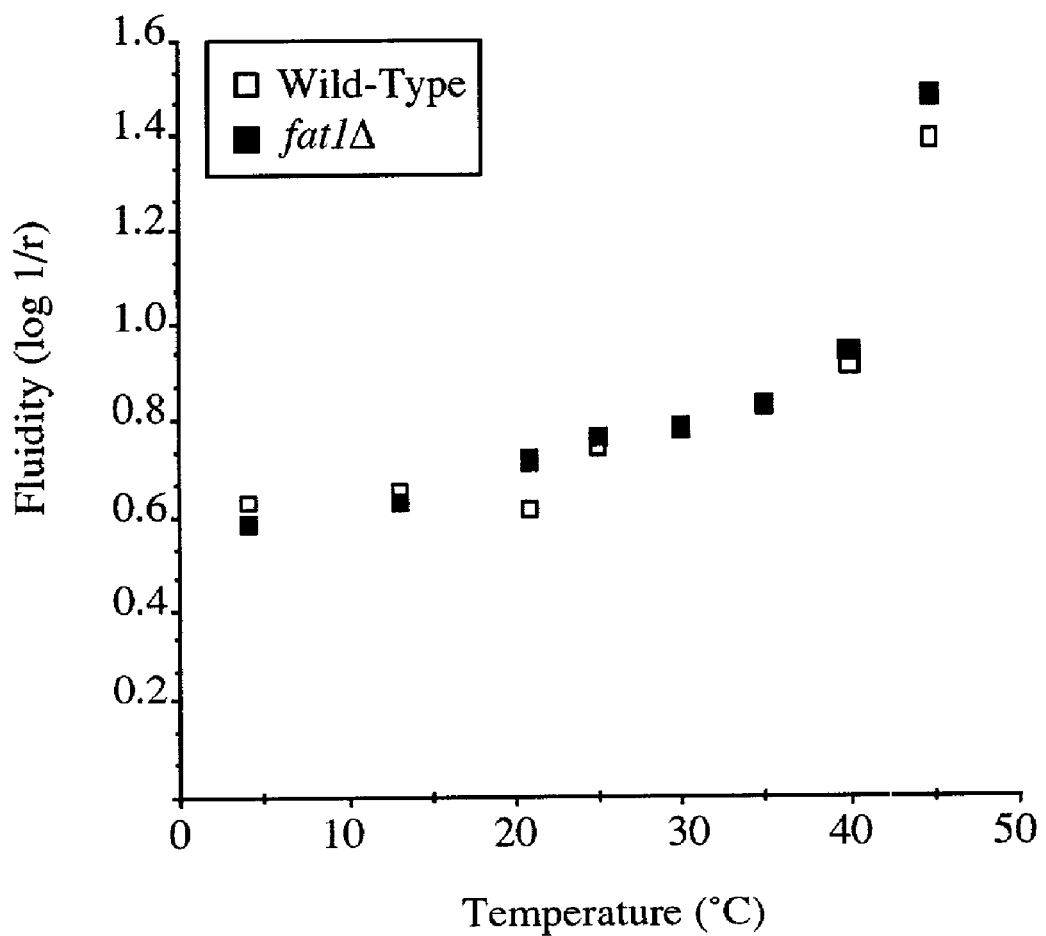

FIG. 9. Membrane fluidity is unchanged in the fat1Δ strain as compared with wild-type. Membrane fluidity of wild-type and fat1Δ cells was monitored using DHP. Fluidity was calculated from the measured anisotropy using the formula: Fluidity=log 1/r, where r is the anisotropy value.

FIGS. 10A and 10B. Localization of Fat1p using a green fluorescent protein (GFP)-Fat1p fusion. The Nomarsky image of yeast cells (W303a transformed with YCpN220 (Fat1p-GFP) (FIG. 10A) that have been imaged for Fat1p-GFP (FIG. 10B), as detailed in Example 1. The small arrows indicate plasma membrane and perinuclear membrane localization of Fat1p; the large arrows indicate lipid bodies.

FIGS. 11A and 11B illustrate data presented in Example 2. Deletion of both FAA1 and FAA4 was required to completely eliminate growth under defined culture conditions (FIG. 11A). This result was comparable to that observed when fatty acid synthase was inhibited with cerulenin (FIG. 11B).

FIGS. 12A, 12B and 12C illustrate data presented in Example 2. Accumulation of exogenous C1-BODIPY-$C_{12}$ was unchanged in the faa4Δ strain or reduced in the faa1Δ strain (FIG. 12A), and further reduced in the faa1Δ faa4Δ strain (FIG. 12B). Centromeric clones (pGALFAA1 and pGALFAA4) encoding these enzymes transformed into the faa1Δ faa4Δ strain led to a large increase in C1-BODIPY-$C_{12}$ accumulation in cells grown in the presence of galactose to induce the expression of Faa1p or Faa4p (FIG. 12C).

Figure 13:
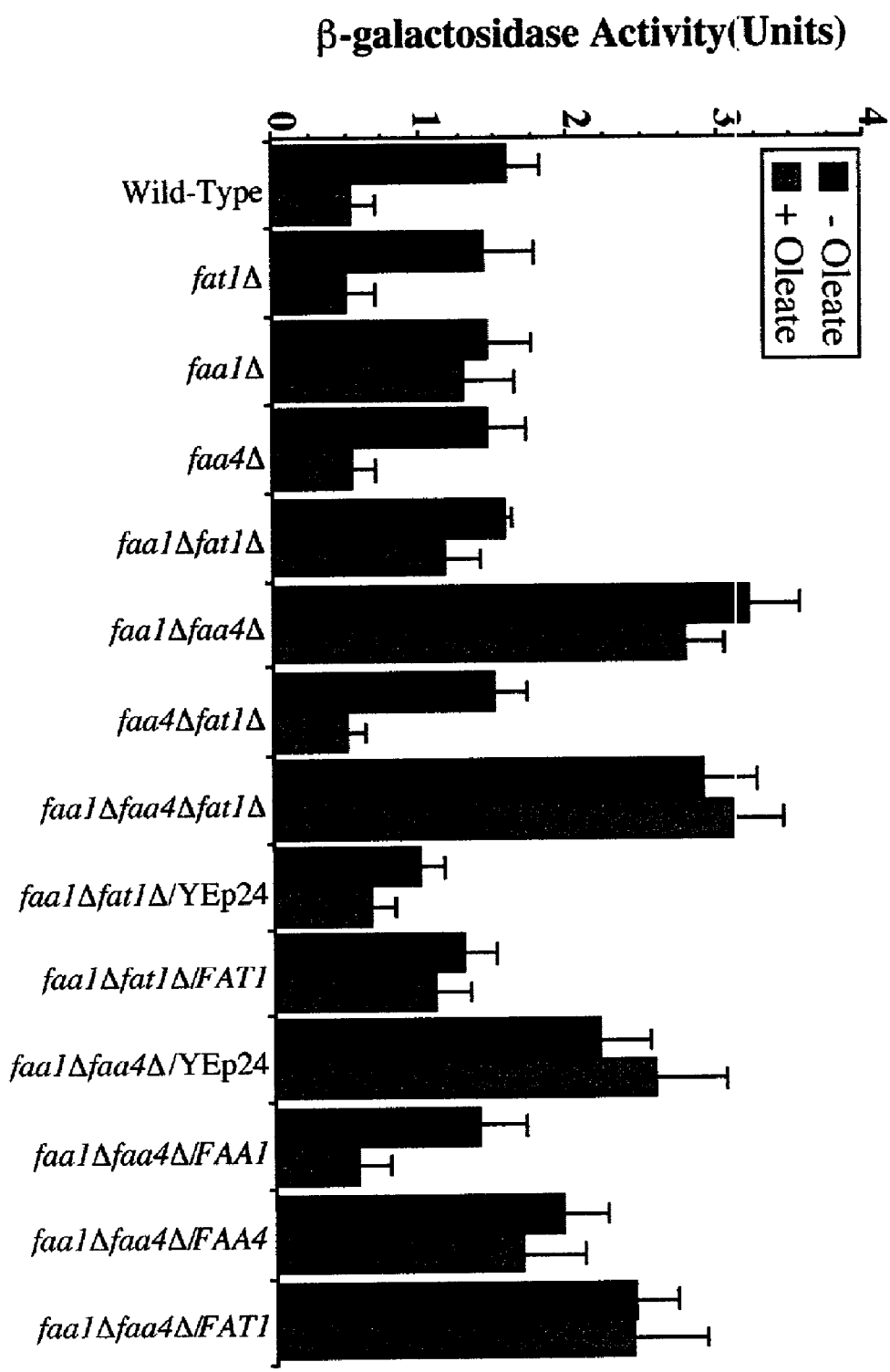

FIG. 13 illustrates data showing no significant difference in oleoyl-CoA levels between cells from the strain deleted for FAA1 alone compared to those with deletions in both FAA1 and FAA4 or all four FAA genes.

Figure 14:
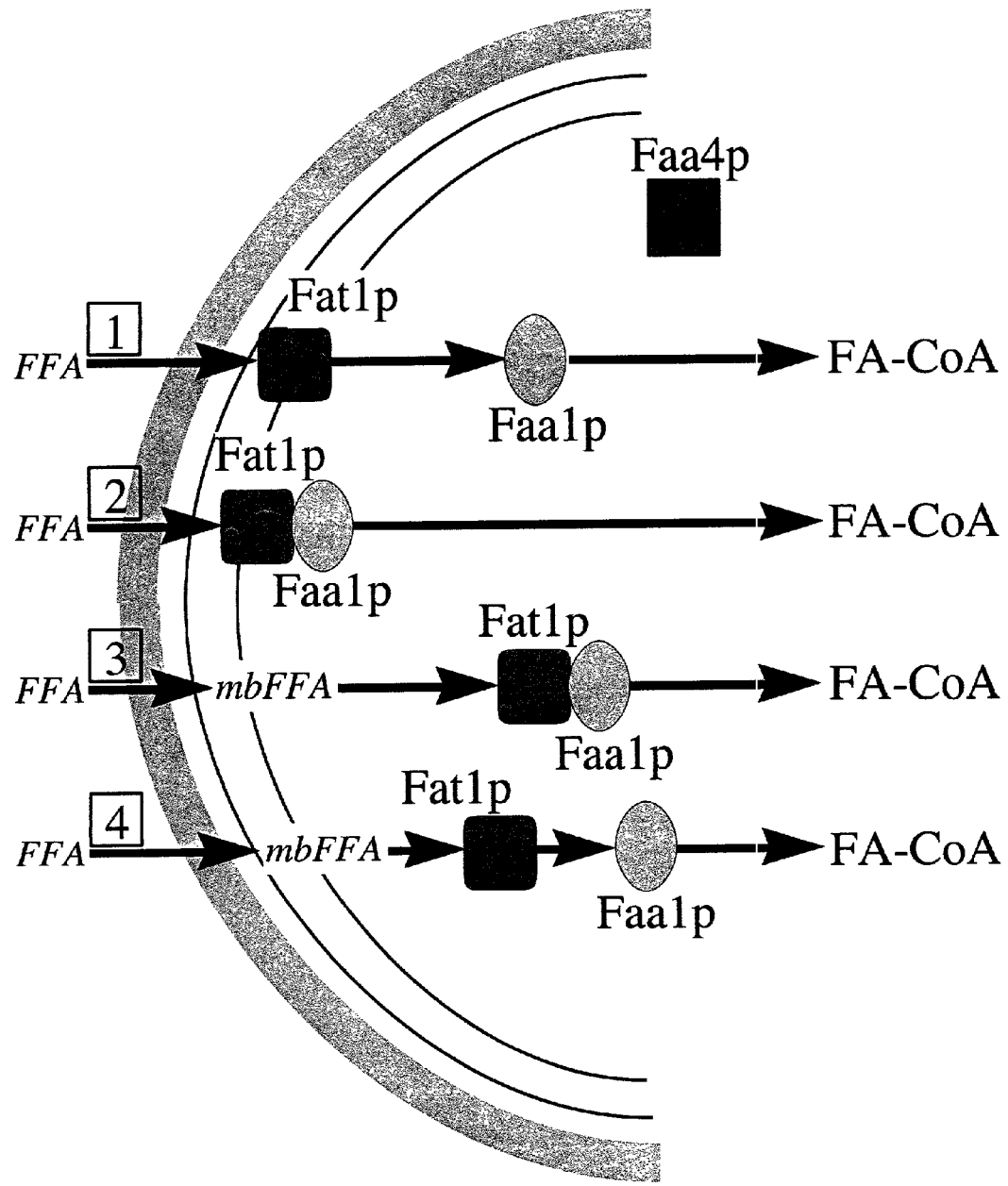

FIG. 14 is a schematic representation depicting TTMp involved in fatty acid transport pathways, as further described in Example 2.

DETAILED DESCRIPTION OF THE INVENTION

The features and other details of the invention will now be more particularly described with reference to the accompanying drawings and pointed out in the claims. The principal features of this invention can be employed in various embodiments without departing from the scope of the invention.

Biological membranes are complex in both their protein and lipid compositions. This complexity is essential and contributes to the barrier function of the membrane and to selectively regulated transport of molecules into and out of the cell. Unlike hydrophilic molecules such as sugars and amino acids, hydrophobic fatty acids, e.g., LCFAs, are able to dissolve in the membrane and, as a consequence, the processes governing their regulated movement across membranes are likely to be quite distinct. Investigations into the problem of fatty acid transport have intensified due to findings that exogenous fatty acids influence a number of important cellular functions, including signaling and transcriptional control. The movement of fatty acids across the membrane is a highly specific and regulated process in various cell types suggesting that in addition to diffusion, there must be other specific mechanisms to facilitate the net movement of these hydrophobic compounds out of the membrane. To date, several distinct membrane-bound and membrane-associated proteins have been identified as components of fatty acid import systems in eukaryotic cells. Most notable amongst these are fatty acid translocase (FAT, the murine orthologue to CD36), fatty acid transport protein (FATP) and fatty acyl CoA synthetase. FAT was identified following protein modification using sulfo-N-succinimidyl oleate while FATP and fatty acyl CoA synthetase were identified using expression cloning. Both FAT and FATP have been claimed to be fatty acid transport proteins. Despite these claims, there has been controversy surrounding the classification of FAT/CD36 and FATP as bona fide integral membrane-bound fatty acid transporters. There remain questions as to whether these proteins actually function as components of a fatty acid delivery system (i.e., FAT/CD36) or as components of a utilization driven fatty acid import system (i.e., FATP), which also includes fatty acyl CoA synthetase. In this regard, proteins identified as required for fatty acid transport may function not as transport proteins per se, but in an alternative manner, perhaps by promoting selectivity and specificity of fatty acid delivery to downstream metabolic events. Thus the two hypotheses, protein-mediated and diffusional, that have been put forward are not necessarily exclusive of each other.

The best-characterized fatty acid transport system is that found in *Escherichia coli*. In this case, the specific integral outer membrane protein, FadL, is required for fatty acid binding and transport across that membrane. The fatty acid ligands must then traverse the bacterial periplasmic space and the inner membrane. No inner membrane proteins have been identified that are required for this process. It is believed that protonated fatty acids traverse the inner membrane by diffusion and are subsequently abstracted from the inner membrane concomitant with activation by fatty acyl CoA synthetase. In this manner, exogenous fatty acids are metabolically trapped as CoA thioesters upon transport, which in turn generates a concentration gradient further driving the system. Overath and colleagues coined the term "vectoral acylation" to describe this process at the time they identified the structural gene for the *E. coli* fatty acyl CoA synthetase (fadD). This postulate was initially expanded as the underlying mechanism driving long-chain fatty acid transport in bacteria. At the time the model of vectoral acylation was proposed, the bacterial fatty acid transporter FadL had not been identified. Our subsequent studies have clearly shown that both FadL and fatty acyl CoA synthetase are required for fatty acid transport in *E. coli*.

Using the yeast Saccharomyces cerevisiae as a model system, the fatty acyl CoA synthetases Faa1p or Faa4p function in the fatty acid transport system presumably by activating exogenous fatty acids concomitant with transport. Also, long-chain fatty acid import in yeast requires Fat1p, the yeast ortholog of the murine FATP1. The mechanism by which Fat1p and the fatty acyl CoA synthetases Faa1p and Faa4p work cooperatively to promote fatty acid import is not yet elucidated but is central to fatty acid uptake and/or import. The situation in yeast appears to more closely exemplify the processes occurring in mammalian cell types. This complexity stems from the finding that two fatty acyl CoA synthetases (Faa1p and Faa4p) and Fat1p all participate in this process. A similar situation appears to be operational in murine adipocytes, where there are data supporting a functional association of FATP with fatty acyl CoA synthetase.

When long-chain fatty acids are supplied in growth media, *Saccharomyces cerevisiae* transports these compounds into the cell by a process that requires Fat1p and either the fatty acyl CoA synthetase Faa1p or Faa4p. Prior to metabolic utilization, exogenous fatty acids must first be activated to their CoA thioesters. In yeast, the fatty acyl CoA synthetase Faa1p accounts for approximately 95% of the myristoyl- and palmitoyl-CoA synthetase activity while the fatty acyl CoA synthetase Faa4p accounts for approximately 2% of the activity toward these substrates. Deletion of FAT1 or FAA1 and FAA4 impairs growth on media supplemented with oleate and cerulenin and under anaerobic conditions. Furthermore, deletion of both FAA1 and FAA4 prevents the incorporation of exogenously supplied fatty acids into phospholipids while deletion of FAT1 reduces the rate of incorporation. Under conditions where Faa1p is inactive or expression of FAA1 is reduced, Faa4p partially compensates for the loss of function. As such, in one embodiment, Faa1p function is predominant in metabolically active to growth stage cells, while Faa4p function is predominant in quiescent phase cells. Even though Faa1p and Faa4p have been suggested to be functionally redundant, Faa1p, rather than Faa4p, plays a more distinct role in fatty acid import. As such, fatty acid import and activation are linked processes.

*Saccharomyces cerevisiae* is an ideal model eukaryote for studying fatty acid transport. Yeast are auxotrophic for unsaturated fatty acids when grown under hypoxic conditions or when the fatty acid synthase inhibitor cerulenin is included in the growth media. The FAT1 gene encodes a protein, Fat1p, which is required for maximal levels of fatty acid import and has an acyl CoA synthetase activity specific for very-long-chain fatty acids suggesting this protein plays a pivotal role in fatty acid trafficking. Fat1p and the murine Fatty Acid Transport Protein (FATP) are functional orthologues. FAT1 is essential for growth under hypoxic conditions and when cerulenin is included in the culture media in the presence or absence of unsaturated fatty acids. FAT1 disruptants (fat1Δ) fail to accumulate the fluorescent long-chain fatty acid analogue C1-BODIPY-$C_{12}$, have a greatly diminished capacity to transport exogenous long-chain fatty acids, and have very long-chain acyl CoA synthetase activities that is 40% wild-type. Expression of either Fat1p or murine FATP from a plasmid in a fat1Δ strain restored these phenotypic and biochemical deficiencies. Fat1p and FATP restored growth of fat1Δ cells in the presence of cerulenin and under hypoxic conditions. Furthermore, fatty acid transport was restored and was found to be chain length specific: octanoate, a medium-chain fatty acid was transported in a Fat1p- and FATP-independent manner while the long-chain fatty acids myristate, palmitate, and oleate required either Fat1p or FATP for maximal levels of transport. Lignoceryl CoA synthetase activities were restored to wild-type levels in fat1Δ strains expressing either Fat1p or FATP. Fat1p or FATP also restored wild-type levels of β-oxidation of exogenous long-chain fatty acids. A green fluorescent protein-Fat1p fusion was primarily localized towards the periphery of the cell (plasma membrane localization) supporting the notion that Fat1p, like FATP is found within the plasma membrane. Thus, Fat1p and FATP are functionally equivalent when expressed in yeast and play a central role in fatty acid trafficking.

Definitions

For convenience, certain terms used in the specification, examples, and appended claims are collected here.

Long chain fatty acids ("LCFAs") include saturated and unsaturated fatty acids (and salts or esters thereof) of $C_6$, preferably $C_8$, to $C_{30}$, more preferably to $C_{24}$, e.g., myristic acid, palmitic acid, stearic acid, oleic acid, linoleic acid, linolenic acid, lignoceric acid, and their salts and/or esters.

The "transport mediators" ("TTM") include genes coding for proteins responsible for fatty acid transport and/or uptake, including FAA1, FAA2, FAA3, FAA4, FAT1, FATP, CD36 and FABP, or orthologs, homologs, isoforms, derivatives, analogs, variants, or fragments thereof, singly or in combination. In a preferred embodiment the TTMs include FAA1 and FAT1, and optionally FAA4.

The "transport mediator proteins" ("TTMp") include proteins responsible for fatty acid transport and/or uptake, including Faa1p, Faa2p, Faa3p, Faa4p, Fat1p, FATP, CD36 and FABP, or orthologs, homologs, isoforms, derivatives, variants, analogs, or fragments thereof, singly or in combination. In a preferred embodiment the TTMps include Faa1p and Fat1p, and optionally Faa4p.

The terms "contacting" and "combining" as used herein in the context of bringing molecules into close proximity to each other, can be accomplished by conventional means. For example, when referring to molecules that are soluble, contacting is achieved by adding the molecules together in a solution. "Contacting" can also be by adding an agent to a test system, such as a vessel or plate containing cells in culture. In one embodiment, the contacting is achieved by adding the molecules together in an agar-based growth medium. "Agent" and "modulator" are used interchangeably herein.

The term "inhibitor" or "antagonist", as used herein, refers to an agent that blocks, diminishes, inhibits, hinders, limits, decreases, reduces, restricts or interferes with fatty acid transport into the cytoplasm of a cell, or alternatively and additionally, prevents or impedes the cellular effects associated with fatty acid transport. The term "enhancer" or "agonist", as used herein, refers to an agent that augments, enhances, up-regulates, activates or increases fatty acid transport into the cytoplasm of a cell. An antagonist will decrease fatty acid concentration, fatty acid metabolism and byproduct levels in the cell, leading to phenotypic and molecular changes. An agonist will increase fatty acid concentration, fatty acid metabolism and byproduct levels in the cell, leading to phenotypic and molecular changes.

The term "modulate" as used herein refers to the ability of a molecule to alter the function of another molecule. Thus, modulate could mean, for example, inhibit, activate, enhance, antagonize, agonize, upregulate, downregulate, induce, or suppress. A modulator has the capability of altering function of its target. Such alteration can be accomplished at any stage of the transcription, translation, expression or function of the protein, so that, for example, modulation of a target gene can be accomplished by modulation of the DNA or RNA encoding the protein, and the protein itself.

"Fatty acid transport and/or uptake" includes the net movement of fatty acids from the external milieu across the cell wall and membrane into the internal milieu.

"Fragments" provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a fall length sequence. Fragments may be derived from any contiguous portion of a nucleic acid or amino acid sequence of choice. "Derivatives" are nucleic acid sequences or amino acid sequences formed from the native compounds either directly or by modification or partial substitution. "Analogs" are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type. "Orthologs" are nucleic acid sequences or amino acid sequences of a particular gene that are derived from different species. "Homologs" are related nucleic acid sequences or amino acid sequences of a particular gene that are derived from the same species. "Isoforms" are nucleic acid sequences or amino acid sequences of a particular gene that differ slightly in their sequence, and are located to the same gene locus in different individuals. Isoforms can include splice variants encoded by the same gene locus. A "domain" is any discrete, continuous part of a polypeptide or nucleic acid sequence that can be equated with a particular function.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to The nucleic acids or proteins of the invention, in various embodiments, by at least about 70%, 80%, or 95% identity (with a preferred identity of 80–95%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below.

The invention relates in an aspect, to compounds that modulate or alter TTM or TTMp function; methods of identifying compounds that bind to a TTM or TTMp, or modulate or alter (enhance or inhibit) TTM or TTMp function; methods of modulating or altering (enhancing or inhibiting) TTM or TTMp function and, thus, LCFA uptake into tissues of a mammal (e.g. human) by administering a compound or molecule (a drug or agent) that increases or reduces TTM or TTMp activity.

In one embodiment, the present invention relates to modulating or altering (enhancing or inhibiting/reducing) LCFA uptake, e.g., in the small intestine and, thus, increasing or reducing the number of calories in the form of fats available to an individual. In another embodiment, the present invention relates to inhibiting or reducing LCFA uptake, e.g., in the small intestine in order to reduce circulating fatty acid levels; that is, LCFA uptake in the small intestine is reduced and, therefore, circulating (blood) levels are not as high as they otherwise would be. These TTM or TTMps are targets for methods and drugs that block their function or activity and are useful in treating obesity, diabetes and heart disease. The ability of these TTM or TTMps, e.g., orthologs of Fat1p and Faa1p, to mediate fat uptake can be modulated or altered (enhanced or inhibited), thus modulating fat uptake in the small intestine. This can be done, for example, by administering to an individual, such as a human or other animal, a modulator of the invention in the small intestine, thus inhibiting LCFA passage into the cells of the small intestine. As a result, fat absorption is reduced and, although the individual has consumed a certain quantity of fat, the LCFAs are not absorbed to the same extent they would have been in the absence of the compound administered.

Thus, one embodiment of this invention is a method of reducing LCFA uptake (absorption), e.g., in the small intestine and, as a result, reducing caloric uptake in the form of fat. A further embodiment is a compound (drug) useful in inhibiting or reducing fat absorption in the small intestine. In another embodiment, the invention is a method of reducing circulating fatty acid levels by administering to an individual a compound that blocks interactions of LCFAs with TTM or TTMp function in the small intestine, thus inhibiting LCFA passage into cells of the small intestine. As a result, fatty acids pass into the circulatory system at a diminished level and/or rate, and circulating fatty acid levels are lower than they would be in the absence of the compound administered. This method is particularly useful for therapy in individuals who are at risk for or have hyperlipidemia. That is, it can be used to prevent the occurrence of elevated levels of lipids in the blood or to treat an individual in whom blood lipid levels are elevated. Also the subject of this invention is a method of identifying compounds that alter TTM or TTMp function (and thus, in the case of TTM or TTMp, alter LCFA uptake).

In another embodiment, the present invention relates to a method of modulating or altering (enhancing or inhibiting) the function of TTMp expressed in the heart. A method of inhibiting TTMp function is useful, for example, in individuals with heart disease, such as ischemia, since reducing LCFA uptake into heart muscle in an individual who has ischemic heart disease, which may be manifested by, for example, angina or heart attack, can reduce symptoms or reduce the extent of damage caused by the ischemia. In this embodiment, a drug that inhibits TTM or TTMp function is administered to an individual who has had or is having a heart attack, to reduce LCFA uptake by the individual's heart and, as a result, reduce the damage caused by ischemia. In a further embodiment, this invention is a method of targeting a compound, such as a therapeutic drug or an imaging reagent, to heart tissue by administering to an individual (e.g., a human) a complex of the compound and a component (e.g., a LCFA or LCFA-like compound) that is bound by a TTMp present in cells of heart tissue. Prophylactic administration of compounds identified by the method of the invention is also contemplated.

In a further embodiment, LCFA uptake by the liver is modulated or altered (enhanced or reduced), in an individual. For example, a drug that inhibits the function of a TTM or TTMp present in liver is administered to an individual who is diabetic, in order to reduce LCFA uptake by liver cells and, thus reduce insulin resistance.

The present invention, thus, provides methods that are useful to alter, particularly reduce, LCFA uptake in individuals and, as a result, to alter (particularly reduce), availability of the LCFAs for further metabolism. In a specific embodiment, the present invention provides methods useful to reduce LCFA uptake and, thus, fatty acid metabolism in individuals, with the result that caloric availability from fats is reduced, and circulating fatty acid levels are lower than they otherwise would be. These methods are useful, for example, as a means of weight control in individuals, (e.g., humans) and as a means of preventing elevated serum lipid levels or reducing serum lipid levels in humans. TTMps expressed in the small intestine are useful targets to be blocked in treating obesity (e.g., chronic obesity) or to be enhanced in treating conditions in which enhanced LCFA uptake is desired (e.g., malabsorption syndrome or other wasting conditions).

Long chain fatty acids (LCFAs) are an important energy source for prokaryotes and eukaryotes and are involved in diverse cellular processes, such as membrane synthesis, intracellular signaling, protein modification, and transcriptional regulation. In developed Western countries, human dietary lipids are mainly diglycerides and triglycerides and account for approximately 40% of caloric intake (Weisburger (1997) *J Am. Diet. Assoc.* 97:S16–S23). These lipids are broken down into fatty acids and glycerol by pancreatic lipases in the small intestine (Chapus et al. (1988) *Biochimie* 70:1223–34); LCFAs are then transported into brush border cells, where the majority is re-esterified and secreted into the lymphatic system as chylomicrons (Green & Riley (1981) *Aust. N. Z. J. Med.* 11:84–90). Fatty acids are liberated from lipoproteins by the enzyme lipoprotein lipase, which is bound to the luminal side of endothelial cells (Scow & Blachette-Mackie (1992) *Mol. Cell. Biochem* 116:181–191). "Free" fatty acids in the circulation are bound to serum albumin (Spector (1984) *Clin. Physiol. Biochem* 2:123–134) and are rapidly incorporated by adipocytes, hepatocytes, and cardiac muscle cells. The latter derive 60–90% of their energy through the oxidation of LCFAs (Neely et al. (1972) *Prog. Cardiovasc. Dis.* 15:289–329). Although saturable and specific uptake of LCFAs has been demonstrated for intestinal cells, hepatocytes, cardiac myocytes, and adipocytes, the molecular mechanisms of LCFA transport across the plasma membrane have remained controversial (Hui & Bemlohr (1997) *Front. Biosci.* 15:d222-31-d231; Schaffer & Lodish (1995) *Trends Cardiovasc. Med.* 5:218–224).

Another aspect of the invention relates to a method of producing a TTMp, or orthologs, homologs, isoforms, variants, analogs, derivatives or fragments thereof, and to expression systems and host cells containing a vector appropriate for expression of a TTMp.

Cells that express a TTMp, or orthologs, homologs, isoforms, variants, analogs, derivatives or fragments thereof, can be made and maintained in culture, under conditions suitable for expression, to produce protein in the cells for cell-based assays, or to produce protein for isolation. These cells can be prokaryotic or eukaryotic. Examples of prokaryotic cells that can be used for expression include *Escherichia coli, Bacillus subtilis* and other bacteria. Examples of eukaryotic cells that can be used for expression include yeasts such as *Saccharomyces cerevisiae, Schizosaccharomyces pombe, Pichia pastoris* and other lower eukaryotic cells, and cells of higher eukaryotes such as those from insects and mammals, such as cells derived from primary cells and cell lines such as CHO, HeLa, 3T3 and BHK cells, preferably COS cells and human kidney 293 cells, and more preferably Jurkat cells. See, e.g., Ausubel et al., eds. Current Protocols in Molecular Biology, Greene Publishing Associates and John Wiley & Sons, Inc., containing Supplements up through Supplement 42, 1998).

In one embodiment, host cells that produce a recombinant TTMp, or orthologs, homologs, isoforms, variants, analogs, derivatives or fragments thereof, a variant, or an ortholog of a TTMp, can be made as follows. A gene encoding a TTMp, variant or a portion thereof can be inserted into a nucleic acid vector, e.g., a DNA vector, such as a plasmid, phage, cosmid, phagemid, virus, virus-derived vector (e.g., SV40, vaccinia, adenovirus, fowl pox virus, pseudorabies viruses, retroviruses) or other suitable replicon, that can be present in a single copy or multiple copies, or the gene can be integrated in a host cell chromosome, BAC or YAC. A suitable replicon or integrated gene can contain all or port of the coding sequence for a TTMp or variant, operably linked to one or more expression control regions whereby the coding sequence is under the control of transcription signals and linked to appropriate translation signals to permit translation. The vector can be introduced into cells by a method appropriate to the type of host cells (e.g., transfection, electroporatian, infection, fusion). For expression from the TTMp gene, the host cells can be maintained under appropriate conditions (e.g., in the presence of inducer and/or regulator normal growth conditions, etc.). Proteins or polypeptides thus produced can be recovered (e.g., from the cells, as in a membrane fraction, from the periplasmic space of bacteria, from culture medium) using suitable techniques. Appropriate membrane targeting signals may be incorporated into the expressed polypeptide. These signals may be endogenous to the polypeptide or they may be heterologous signals.

Polypeptides thus produced can be recovered and purified from cell cultures (or from their primary cell source) by well-known methods including amnmonium sulfate or ethanol precipitation, acid extraction, anion or cation exchange chromatography, phosphocellulose chromatography, hydrophobic interaction chromatography, affinity chromatography, hydroxylapatite chromatography and high performance liquid chromatography. Known methods for refolding protein can be used to regenerate active conformation if the polypeptide is denatured during isolation or purification.

In a further aspect of the invention are methods for assessing the function of any of the TTMps described herein, including orthologs, homologs, isoforms, variants, analogs, derivatives or fragments thereof, and in variations of these, methods for identifying an inhibitor (or an enhancer) of such function and methods for assessing the TTMp function in the presence of a candidate inhibitor or a known inhibitor or a candidate enhancer or a known enhancer.

A variety of systems comprising living cells can be used for these methods. Cells to be used in fatty acid transport assays, and further in methods for identifying an inhibitor or enhancer of this function, express one or more TTMps. Cells for use in cell-based assays described herein can be drawn from a variety of sources, such as isolated primary cells of various organs and tissues wherein one or more TTMps are naturally expressed. In some cases, the cells can be from adult organs, and in some cases, from embryonic or fetal organs, such as heart, lung, liver, intestine, skeletal muscle, kidney and the like. Cells for this purpose can also include cells cultured as fragments of organs or in conditions simulating the cell type and/or tissue organization of organs, in which artificial materials may be used as substrates for cell growth. Other types of cells suitable for this purpose include cells of a cell strain or cell line (ordinarily comprising cells considered to be "transformed") modified to express one or more TTMps. Suitable cell types are detailed above.

Isolated fatty acid transport protein, or an antigenically similar portion thereof, especially a portion that is soluble, can be used in a method to select and identify molecules that bind specifically to the TTMp. In another embodiment of the method, fusion proteins comprising all of, or a portion of, the fatty acid transport protein licked to a second moiety not occurring in the TTMp as found in nature, can be prepared for use. Suitable fusion proteins for this purpose include those in which the second moiety comprises an affinity ligand (e.g., an enzyme, antigen, epitope). TTMp fusion proteins can be produced by the insertion of a gene encoding the TTMp or a variant thereof, or a suitable portion of such gene into a suitable expression vector, e.g., one that encodes an affinity ligand (e.g., pGEX-4T-2 and pET-15b, encoding glutathione S-transferase and His-Tag affinity ligands, respectively). The expression vector can be introduced into a suitable host cell for expression. Host cells are lysed and the lysate, containing fusion protein, can be bound to a suitable affinity matrix by contacting the lysate with an affinity matrix. Other methods for protein production and purification are known in the art and are contemplated as within the scope of the invention.

In one embodiment, the fusion protein can be immobilized on a suitable affinity matrix under conditions sufficient to bind the affinity ligand portion of the fusion protein to the matrix. The TTMp portion of the bound fusion protein is then contacted with one or more candidate binding agents (e.g., a mixture of peptides) to be tested, under conditions suitable for binding of the binding agents to the TTMp portion of the bound fusion protein. Next, the affinity matrix with bound fusion protein can be washed with a suitable wash buffer to remove unbound candidate binding agents and non-specifically bound candidate binding agents. Those agents that remain bound can be released by contacting the affinity matrix with fusion protein bound thereto with a suitable elution buffer. Wash buffer can be formulated to permit binding of the fusion protein to the affinity matrix, without significantly disrupting, binding of specifically bound binding agents. In one aspect, elution buffer can be formulated to permit retention of the fusion protein by the affinity matrix, but can be formulated to interfere with binding of the candidate binding agents to the target portion of the fusion protein. For example, a change in the ionic strength or pH of the elution buffer can lead to release of specifically bound agent, or the elution buffer can comprise a release component or components designed to disrupt binding of specifically bound agent to the target portion of the fusion protein.

The invention also comprises a method for identifying an agent that inhibits fatty acid transport, i.e., a modulator of TTMp. The TTMp can be one described by an amino acid sequence herein, a portion or fragment thereof, a variant thereof, or orthologs, homologs, isoforms, variants, analogs, derivatives or fragments thereof, or a TTMp fusion protein. One method comprises: (a) combining various components, not limited to a particular order, such as a TTMp protein, the ligand of the TTMp protein, and a candidate agent to be assessed for its ability to modulate the action of the TTMp for fatty acid uptake (e.g., pH, salt, temperature conditions conducive to appropriate conformation and molecular interactions); (b) determining the extent to which the protein and ligand interact; and (c) comparing (1) the extent of protein-ligand interaction in the presence of candidate agent with (2) the extent of protein-ligand interaction in the absence of candidate agent, wherein if (1) is less than (2), then the candidate agent is one that inhibits interaction between the protein and the ligand. In the alternative, if (1) is greater than (2), then the candidate agent is one that enhances interaction between the protein and the ligand.

In a further embodiment, an inhibitor (or an enhancer) of a fatty acid transport protein can be identified. The method comprises steps that include, or are variations of, the following: contacting the test system with fatty acid, wherein the fatty acid can be labeled for convenience of detection; contacting a first aliquot of the cells with an agent being tested as an inhibitor (or enhancer) of fatty acid uptake while maintaining a second aliquot of cells under the same conditions but without contact with the agent; and measuring (e.g., quantitating) fatty acid in the first and second aliquots of cells; wherein a lesser quantity of fatty acid in the first aliquot compared to that in the second aliquot is indicative that the agent is an inhibitor of fatty acid uptake by a fatty acid transport protein. A greater quantity of fatty acid in the first aliquot compared to that in the second aliquot is indicative that the agent is an enhancer of fatty acid uptake by a fatty acid transport protein. In the alternative, enhancement or inhibition of cell growth under conditions suitable to induce growth dependence or sensitivity to the presence of fatty acids in the cell so contacted. Increase in growth indicates an enhancer of TTMp activity. Death, decreased cell growth or lack of cell growth indicates an inhibitor of TTMp activity. In vitro systems may also be employed in a manner familiar to those skilled in the art.

A particular embodiment of identifying an inhibitor or enhancer of fatty acid transport function employs the above steps, but also employs additional steps preceding those given above: introducing into a cell of a cell strain or cell line ("host cells" for the intended introduction of, or after the introduction of, a vector) a vector comprising a fatty acid transport protein gene, wherein expression of the gene can be regulatable or constitutive, and providing conditions to the host cells under which expression of the TTM gene can occur.

In order to produce a "host cell" type suitable for fatty acid uptake assays and for assays derived therefrom for identifying inhibitors or enhancers thereof, a nucleic acid vector can be constructed to comprise a gene encoding a TTMp, a mutant or variant thereof, an ortholog of the human proteins, such as mouse orthologs or orthologs found in other mammals, or a TTMp family protein of origin in an organism other than a mammal. The gene of the vector can be regulatable, such as by the placement of the gene under the control of an inducible or repressible promoter in the vector (e.g., inducible or repressible by a change in growth conditions of the host cell harboring the vector, such as addition of inducer, binding or functional removal of repressor from the cell milieu, or change in temperature) such that expression of the TTMp gene can be turned on or initiated by causing a change in growth conditions, thereby causing the protein encoded by the gene to be produced, in host cells comprising the vector, as a plasma membrane protein. Alternatively, the TTMp gene can be constitutively expressed.

Yeast cells can be used in a similar cell-based assay for the uptake of fatty acids mediated by a TTMp, and such an assay can be adapted to a screening assay for the identification of agents that inhibit or enhance fatty acid uptake by a TTMp. Yeast cells lacking an endogenous TTM or TTMp activity (mutated, disrupted or deleted for FAT1. See, e.g., Faergeman et al., (1997) *J. Biol. Chem.* 272(13):8531–8538; Watkins et al., (1998) *J. Biol. Chem.* 273(29):18210–18219) can be engineered to harbor a related orthologous or homologous gene of the family of TTMp-encoding genes, such as a mammalian, e.g., human, TTM or TTMp.

Examples of yeast expression vectors include pEG (Mitchell et al., (1993) *Yeast* 9:715–10 723) and pDAD1 and pDAD2, which contain a GAL1 promoter. See, Davis and Fink (1990) *Cell* 61:965–978. A variety of promoters are suitable for expression. Available yeast vectors offer a choice of promoters. In one embodiment, the inducible GAL1 promoter is used. In another embodiment, the constitutive ADH1 promoter (alcohol dehydrogenase; Bennetzen and Hall (1982) *J. Biol. Chem.* 257:3026–3031) can be used to express an inserted gene on glucose-containing media. An example of a vector suitable for expression of a heterologous TTM or TTMp gene in yeast is pQB169. Additional expression vectors are well known to those in the art and are within the scope of this invention. Such vectors include those suitable for expression in yeast, including *Saccharomyces cerevisiae* and *Schizosaccharomyces pombe*.

With the introduced TTM gene providing the only fatty acid transport protein function for a yeast cell, it is possible to study the effect of the heterologous TTMp on fatty acid transport into the yeast cells in isolation. Assays for the uptake of fatty acids into the yeast cells can be devised that are similar to those described above and/or those assays that have been illustrated in the Examples. Assays include analysis of accumulation of labeled fatty acid derivatives, modulation of cell growth, or cell death. Tests for candidate inhibitors or enhancers of the heterologous TTM or TTMp can be done in cultures of yeast cells, wherein the yeast cells are incubated with fatty acid substrate and an agent to be tested as an inhibitor or enhancer of TTM or TTMp function. TTM or TTMp uptake after a period of time can be measured by analyzing the contents of the yeast cells for fatty acid substrate, as compared with control yeast cells incubated with the fatty acid, but not with the test agent. Yeast cells have the additional advantage, over mammalian cells in culture, for example, that yeast cells can be forced to rely upon fatty acids as their only source of carbon, if the growth medium supplied to the yeast cells is formulated to contain no other source of carbon. Thus, the effect of the heterologous TTM or TTMp on fatty acid uptake and metabolism in the engineered yeast cells can be amplified. An agent that efficiently blocks transport function of the heterologous TTM or TTMp could result in death of the yeast cells. Thus, in this case, inhibition of function of the heterologous TTM or TTMp can result in loss of viability. A simple, measure of viability is turbidity of the yeast suspension culture, which can be adapted to a high throughput screening assay for effects of various agents to be tested, using microtiter plates or similar devices for small-volume cultures of the engineered yeast cells.

It is preferred that the TTMp whose function is to be assessed, with or without a candidate inhibitor or enhancer, is cloned from the TTMp gene of the same or related species in which the modulator identified by the method of the invention will be used, especially where use is prophylactic or therapeutic. For example, it is preferable that the TTMp to be tested is encoded by a TTM gene cloned from a mammalian subject, e.g., a human, where modulators are being screen as therapeutic drug targets for use in mammalian subjects, e.g. a human subject. Preferably, screening for modulators of a chosen TTMp will be carried out in a non-mammalian cell producing the TTMp, preferably a bacterial cell or yeast cell. Most preferably, the cell will be a yeast cell, wherein the endogenous yeast TTM is non-functional, i.e., mutated, deleted or altered, and the exogenous TTMp is a mammalian ortholog functioning to reconstitute the fatty acid transport system, thereby providing a more sensitive screen with lower background noise. In one embodiment, the screening and assays are done in a high throughput screening system.

A vector comprising a TTMp gene, such as a vector described herein, can be introduced into host cells by a means appropriate to the vector and to the host cell type. For example, commonly used methods such as electroporation, transfection, for instance, transfection using $CaCl_2$, and transduction (as for a virus or bacteriophage) can be used. Host cells can be, for example, mammalian cells such as primary culture cells or cells of cell lines such as COS cells, 293 cells or Jurkat cells. Host cells can also be prokaryotic or eukaryotic. Examples of prokaryotic cells that can be used for expression include *Escherichia coli, Bacillus subtilis* and other bacteria. Examples of eukaryotic cells that can be used for expression include yeasts such as *Saccharomyces cerevisiae, Schizosaccharomyces pombe, Pichia pastoris* and other lower eukaryotic cells, and cells of higher eukaryotes such as those from insects, such as SfP9 insect cells. Examples of mammalian cells further include primary cells and cell lines such as CHO, HeLa, 3T3 and BHK cells, preferably COS cells and human kidney 293 cells, and more preferably Jurkat cells.

A TTMp whose function is to be assessed, with or without a candidate inhibitor or enhancer, can be produced in host cells whose ancestor cells originated in a species related to the species of origin of the TTMp gene encoding the fatty acid transport protein. For example, tests of function or of inhibition or enhancement of a mammalian TTM can be carried out in host mammalian cells producing the TTMp, rather than bacterial cells or yeast cells.

Host cells comprising a vector comprising a regulatable TTMp gene can be treated so as to allow expression of the TTMp gene and production of the encoded protein (e.g., by contacting the cells with an inducer compound that effects transcription from an inducible promoter operably linked to the TTMp gene).

The test agent (e.g., an agonist or antagonist) is added to the cells to be used in a fatty acid transport assay, in the presence or absence of a test agent, under conditions suitable for production and/or maintenance of the expressed TTMp in a conformation appropriate for association of the TTMp with test agent and substrate. For example, conditions under which an agent is assessed, such as media and temperature requirements, can, initially, be similar to those necessary for transport of typical fatty acid substrates across the plasma membrane. One of ordinary skill in the art will know how to vary experimental conditions depending upon the biochemical nature of the test agent. The test agent can be added to the cells in the presence of fatty acid, or in the absence of fatty acid substrate, with the fatty acid substrate being added following the addition of the test agent. The concentration at which the test agent is evaluated can be varied, as appropriate, to test for an increased effect with increasing concentrations.

Test agents to be assessed for their effects on fatty acid transport can be any chemical (element, molecule, compound), made synthetically, made by recombinant techniques or isolated from a natural source. For example, test agents can be peptides, polypeptides, peptoids, sugars, hormones, or nucleic acid molecules, such as antisense nucleic acid molecules. In addition, test agents can be small molecules or molecules of greater complexity made by combinatorial chemistry, for example, and compiled into libraries. These libraries can comprise, for example, acids, alcohols, alkyl halides, amines, amides, esters, aldehydes, ethers and other classes of organic compounds. Test agents can also be natural or genetically engineered products isolated from lysates of cells, bacterial, animal or plant, or can be the cell lysates themselves. Presentation of test compounds to the test system can be in either an isolated form or as mixtures of compounds, especially in initial screening steps.

Thus, the invention relates to a method for identifying agents that alter fatty acid transport, the method comprising providing the test agent to the cell (wherein "cell" includes the plural, and can include cells of a cell strain, cell line or culture of primary cells or organ culture, for example), under conditions suitable for binding to its target, whether to the TTM or TTMp itself or to another target on or in the cell, wherein the transformed cell comprises a TTM or TTMp.

In greater detail, to test one or more agents or compounds (e.g., a mixture of compounds that can conveniently be screened initially) for modulators of the transport function of a fatty acid transport protein, the agent(s) can be contacted with the cells. In certain embodiments, a "first" aliquot of cells (called "test" cells) can be contacted with a labeled fatty acid. The fatty acid can be, for example, a known substrate of the fatty acid transport protein such as oleate or palmitate. The fatty acid can itself be labeled with a radioactive isotope, (e.g., $^3$H or $^{14}$C) or can have a radioactively labeled adduct attached. In other variations, the fatty acid can have chemically attached to it a fluorescent label, or a substrate for an enzyme occurring within the cells, wherein the substrate yields a detectable product, such as a highly colored or fluorescent product. Addition of candidate inhibitors and labeled substrate to the cells comprising fatty acid transport protein can be in either order or can be simultaneous.

A second aliquot of cells (called "control" cells) is treated, if necessary (as in the case of transformed "host" cells), so as to allow expression of the TTMp encoded by the TTM gene, and is contacted with the labeled substrate of the fatty acid transport protein. The second aliquot of cells is not contacted with one or more agents to be tested for modulation of the transport function of the protein produced in the cells, but is otherwise kept under the same culture conditions as the first aliquot of cells.

In a further step of a method to identify inhibitors of a fatty acid transport protein, the labeled fatty acid is measured in the first and second aliquots of cells. A preliminary step of this measurement process can be to separate the external medium from the cells so as to be able to distinguish the labeled fatty acid external to the cells from that which has been transported inside the cells. This can be accomplished, for instance, by removing the cells from their growth container, centrifuging the cell suspension, removing the supernatant and performing one or more wash steps to extensively dilute the remaining medium that may contain labeled fatty acid. Detection of the labeled fatty acid can be by a means appropriate to the label used. For example, for a radioactive label, detection can be by scintillation counting of appropriately prepared samples of cells (e.g., lysates or protein extracts); for a fluorescent label, by measuring fluorescence in the cells by appropriate instrumentation.

If a compound tested as a candidate modulator of transport function causes the test cells to have less labeled fatty acid detected in the cells than that detected in the control cells, then the compound is an inhibitor of the fatty acid transport protein. Procedures analogous to those above can be devised for identifying enhancers (agonists of TTMps) of fatty acid transport function wherein if the test cell contains more labeled fatty acid than that detected in the control cell, or if the fatty acid is taken up at a higher rate, then the compound being tested is concluded to be an enhancer of the fatty acid transport protein.

Another assay to determine whether an agent is an inhibitor (or enhancer) of fatty acid transport employs animals, one or more of which are administered the agent, and one or more of which are maintained under similar conditions, but are not administered the agent. Both groups of animals are given fatty acids (e.g., orally, intravenously, by tube inserted into stomach or intestine), and the fatty acids taken up into a bodily fluid (e.g., serum) or into an organ or tissue of interest are measured from comparable samples, taken from each group of animals. The fatty acids may carry a label (e.g., radioactive) to facilitate detection and quantitation of fatty acids taken up into the fluid or tissue being sampled. This type of assay can be used alone or can be used in addition to in vitro assays of a candidate inhibitor or enhancer.

An agent determined to be an inhibitor (or enhancer) of TTMp function, such as fatty acid binding and/or fatty acid uptake, can be administered to cells in culture, or in vivo, to a mammal (e.g. human) to inhibit (or enhance) TTMp function. Such an agent may be one that acts directly on the TTMp (for example, by binding) or can act on an intermediate in a biosynthetic pathway to produce TTMp, such as transcription of the TTMp gene, processing of the mRNA, or translation of the mRNA. An example of such an agent is antisense oligonucleotide.

In assays similar to those described above, a candidate inhibitor or enhancer of fatty acid transport function can be added (or mock-added, for control cultures) to cultures of cells engineered to express a desired TTMp to which fatty acid substrate is also added. Inhibition of fatty acid uptake is indicated by a lack of the drop in pH, indicating fatty acid uptake, that is seen in control cells. Enhancement of fatty acid uptake is indicated by a decrease in intracellular pH, as compared to control cells not receiving the candidate enhancer of fatty acid transport function.

Cell-free assays can also be used to measure the transport of fatty acids across a membrane, and therefore also to assess a test treatment or test age at for its effect on the rate or extent of fatty acid transport. An isolated TTMp, for example in the presence of a detergent that preserves the native 3-dimensional structure of the TTMp, or partially purified TTMp, can be used in an artificial membrane system typically used to preserve tile native conformation and activity of membrane proteins. Such systems include liposomes, artificial bilayers of phospholipids, isolated plasma membrane such as cell membrane fragments, cell membrane fractions, or cell membrane vesicles, and other systems in which the TTMp can be properly oriented within the membrane to have transport activity. Assays for transport activity can be performed using methods analogous to those that can be used in cells engineered to predominantly express one TTMp whose function is to be measured. A labeled (e.g., radioactively labeled) fatty acid substrate can be incubated with one side of a bilayer or in a suspension of liposomes constructed to integrate a properly oriented TTMp. The accumulation of fatty acids with time can be measured, using appropriate means to detect the label (e.g., scintillation counting of medium on each side of the bilayer, or of the contents of liposomes isolated from the surrounding medium). Assays such as these can be adapted to use for the testing of agents that might interact with the TTMp to produce an inhibitory or an enhancing effect on the rate or extent of fatty acid transport. That is, the above-described assay can be done in the presence or absence of the agent to be tested, and the results compared.

For examples of isolation of membrane proteins (ADP/ATP carrier and uncoupling protein), reconstitution into phospholipid vesicles, and assays of transport. See Klingenberg et al., *Methods Enzymol.* 260:369–389 (1995). For an example of a membrane protein (phosphate carrier of *Saccharomyces cerevisiae*) that was purified and solubilized from *E. coli* inclusion bodies. See Schroer et al., *J. Biol. Chem.* 273: 14269–14276 (1998). The Glut1 glucose transporter of rat has been expressed in yeast. A crude membrane fraction of the yeast was prepared and reconstituted with soybean phospholipids into liposomes. Glucose transport activity could be measured in the liposomes. See, Kasahara and Kasahara, (1998) *J. Biol. Chem.* 273: 29113–29117. Similar methods can be applied to the proteins and polypeptides of the invention.

Another embodiment of the invention is a method for inhibiting fatty acid uptake in a mammal (e.g., a human), comprising administering to the mammal a therapeutically effective amount of an inhibitor of the transport function of one or more of the fatty acid transport proteins, thereby decreasing fatty acid uptake by cells comprising the fatty acid protein(s). Where it is desirable to reduce the uptake of fatty acids, for example, in the treatment of chronic obesity or as a part of a program of weight control or hyperlipidemia control in a human, one or more inhibitors of one or more of the fatty acid transport proteins is administered in an effective dose, and by an effective route, for example, orally, or by an indwelling device that can deliver doses to the small intestine. The inhibitor can be one identified by methods described herein, or can be one that is, for instance, structurally related to an inhibitor identified by methods described herein (e.g., having chemical adducts to better stabilize or solubilize the inhibitor). The invention further relates to compositions comprising inhibitors of fatty acid uptake in a mammal, which may further comprise pharmaceutical carriers suitable for administration to a subject mammal, such as sterile solubilizing or emulsifying agents.

The invention also relates to compositions comprising a modulator of TTMp function. Antagonists or agonists (inhibitors or enhancers) of the TTMps of the invention, antibodies that bind a TTMp, or mimetics of a TTMp can be employed in combination with a non-sterile or sterile carrier or carriers for use with cells, tissues or organisms, such as a pharmaceutical carrier suitable for administration to a mammalian subject. Such compositions comprise, for instance, a media additive or a therapeutically effective amount of am inhibitor or enhancer compound to be identified by an assay of the invention and a pharmaceutically acceptable carrier or excipient. Such carriers may include, but are not limited to, saline, buffered saline, dextrose, water, ethanol, surfactants, such as glycerol, excipients such as lactose and combinations thereof. The formulation can be chosen by one of ordinary skill in the art to suit the mode of administration. The chosen route of administration will be influenced by the predominant tissue or organ location of the TTMp whose function is to be inhibited or enhanced. For example, administration can be oral or through a tube inserted into the stomach (e.g., direct stomach tube or nasopharyngeal tube), or through other means to accomplish delivery to the small intestine. The invention further relates to diagnostic and pharmaceutical packs and kits comprising one or more containers filled with one or more of the ingredients of the aforementioned compositions of the invention.

Compounds of the invention that are TTMps, TTMp fusion proteins, TTMp mimetics, TTMp gene-specific antisense poly- or oligonucleotides, inhibitors or enhancers of a TTMp may be employed alone or in conjunction with other compounds, such as therapeutic compounds. The pharmaceutical compositions may be administered in any effective, convenient manner, including administration by topical, oral, anal, vaginal, intravenous, intraperitoneal, intramuscular, subcutaneous, intranasal, transdermal or intradermal routes, among others. In therapy or as a prophylactic, the active agent may be administered to an individual as an injectable composition, for example as a sterile aqueous dispersion, preferably isotonic.

Alternatively, the composition may be formulated for topical application, for example, in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions.

In addition, the amount of the compound will vary depending on the size, age, body weight-manipulation of established dose ranges are well within the ability of those of skill in the art.

The invention is further illustrated by the following examples, which are not intended to be limiting in any way.

EXAMPLES

Example 1

One model of uptake of exogenous long-chain fatty acids across the plasma membrane suggests that long-chain fatty acids freely diffuse across the membrane thereby obviating the need for any type of transporter. In this case, uptake is thought to be regulated either at the level of fatty acid delivery to the membrane or by subsequent metabolic utilization of the fatty acid. The second model hypothesizes one or more specific membrane-bound proteins facilitate the transport of long-chain fatty acids across the membrane. The identification of specific membrane-bound proteins that participate in the transport of exogenous long-chain fatty acids is consistent with the findings that this process is highly regulated in different cell types. Three main classes have been described in eukaryotic cells: Fatty Acid Translocase (FAT), Fatty Acid Binding Protein—plasma membrane-bound (FABPpm), and Fatty Acid Transport Protein (FATP).

The FATP-family encompasses a highly conserved group of membrane proteins identified within the last five years with at least two proposed functions. The role first associated with FATP is the transport of long-chain fatty acids across the plasma membrane. The second activity associated with FATP is very long-chain acyl-CoA synthetase activity (VLACS). Homologies between murine FATP, the yeast homologue Fat1p and the AMP-forming acyl-CoA synthetase family of enzymes were noted when the genes were first cloned. Subsequent analyses of yeast strains deficient in Fat1p (fat1Δ) indicated they were compromised in their ability to import fatty acids supporting the conclusion for a transport function. Recently, it was demonstrated that fat1Δ strains accumulate very long-chain fatty acids in the absence of exogenous fatty acids implicating a role for this protein in endogenous fatty acid synthesis and/or degradation, perhaps, due specifically to the decrease in VLACS activity.

Yeast strains containing a deletion in the structural gene for Fat1p (fat1Δ) can be distinguished from the wild-type cells on the basis of a number of biochemical and growth phenotypes. These strains (i) are compromised in their ability to grow on media containing the fatty acid synthesis inhibitor cerulenin and long-chain fatty acids; (ii) show reduced uptake of radioactively labeled long-chain fatty acids; and (iii) fail to accumulate the fluorescent long-chain fatty acid analogue C1-BODIPY-$C_{12}$. Collectively, these data support the hypothesis that Fat1p plays a significant role in the import, metabolism and utilization of long-chain fatty acids. As supported below, Fat1p is the functional orthologue of the mammalian fatty acid transport protein FATP.

Materials and Methods

Strains and Media

The isogenic Saccharomyces cerevisiae strains W303a (leu2, ura3, trp1, ade2, his3), W303a-fat1Δ-1 (leu2, ura3, trp1, ade2, his3, FAT1::HIS3) and W303a Ade+ (leu2, ura3, trp1, his3) were used in all of the experiments described. Construction of W303a-fat1Δ-1 was described in J. Biol. Chem., 272, 8531–8538. YPD media consisted of 1% yeast extract, 2% peptone, and 2% dextrose. Minimal media (YNBD) contained 0.67% yeast nitrogen base, 2% dextrose, adenine (20 mg/l), uracil (20 mg/l) and amino acids as required for either the gene replacement experiments or the complementation experiments (arginine, tryptophan, histidine, and tyrosine (20 mg/l); lysine (30 mg/l); and leucine (100 mg/l)). To assess growth when fatty acid synthase was inhibited, cells were grown on solid YNBD supplemented with 45 μM cerulenin, 50 μM oleate and amino acids and uracil as required (YNBD-CER-OLE). To assess growth under hypoxic conditions cells were grown in an anaerobic chamber on solid YNBD supplemented with 20 μg/ml ergosterol (YNBDE), 50 μM oleate, and amino acids and uracil as required (YNBDEO).

Construction of FAT1 and FATP Complementing Clones

S. cerevisiae genomic DNA from strain UCC1023 was isolated and purified using standard techniques and served as a template for PCR amplification of the FAT1 gene. PCR amplification was performed using the UlTma™ DNA polymerase (Perkin Elmer) with the forward primer 5'-CAGGT-TCTTGCTTGTCTTTGG-3' (SEQ ID NO: 1) and the reverse primer 5'-GGAGTGAGA-AGGATGCTCTAA-3' (SEQ ID NO: 2). The FAT1 sequence is based on the corrected sequence reported by Watkins et al., J. Biol. Chem., 273, 18210–18219 and verified in this work. The resulting 2.1 kb amplicon was TA cloned into pCR2-1 (Invitrogen) yielding pDB101. A Xho1/Spe1 fragment from pDB101, containing the FAT1 gene and its native promoter region, was subcloned into pRS316 (J. Biol. Chem., 272, 8531–8538) to produce pDB102. The FATP cDNA in pBlue-Script SK+ (Stratagene) was subcloned behind the constitutive glyceraldehyde-3-phosphate dehydrogenase (GPD) promoter as a BamH1/Not1 fragment into pBB358, to produce pDB104. pBB358 is a derivative of pRS316 containing the GPD promoter and was kindly provided by Jeffrey I. Gordon (Washington University School of Medicine, St. Louis, Mo., USA). Strains were rendered competent by lithium acetate using standard procedures and transformed with pRS316, pDB102 (FAT1), or pDB104 (FATP).

Construction and Expression of GFP-FAT1

The FAT1 coding sequence was PCR amplified using a pair of oligonucleotides, (5'CGCGGATCCATGTCTC-CCATACAGGTT3' (SEQ ID NO: 3) containing a BamH1 site at +1 of translation of FAT1 and 5'AAGCTCGAGT-GATAATTTAATTGTTTGTGCATCG3' (SEQ ID NO: 4) containing an Xho1 site at the termination of the FAT1 coding sequence) and high fidelity Taq polymerase using reaction conditions recommended by the supplier (Roche Molecular Biochemicals). The amplicon was digested with BamH1 and Xho1 and ligated into the N-terminal GFP fusion vector pUG36 (kindly provided by J. Hegemann) to generate pDB220 in which expression of the GFP-FAT1 fusion is regulated by the MET25 promoter. See, Niedenthal et al. (1996) Yeast, 12, 773–86. The in-frame fusion between the amino-terminal green fluorescent protein and FAT1 was confirmed by dideoxy sequencing. pDB220 was transformed into W303a Ade+ and selected for uracil prototrophs. For localization studies transformed cells were inoculated over night in YNBD plus amino acids as required (minus methionine and uracil) and diluted in fresh media to an $OD_{600}$ of 0.05 and grown to an $OD_{600}$ of 0.6. Cells were harvested by centrifugation, supernatant aspirated off except for ~50 μl in which the cells were resuspended. Cells were visualized using a Noran-OZ confocal laser scanning microscope (OZ CLSM) system.

C1-BODIPY-$C_{12}$-labeled Fatty Acid Uptake and Time-lapse Imaging

Following cell growth, washed cells were attached to a poly-lysine coated coverslip and placed in a closed bath imaging perfusion chamber (Warner Instrument Corp.). The immobilized cells were superfused with phosphate buffered saline (PBS) and a field of cells was identified by conventional light microscopy prior to collection of fluorescent images. Cells were imaged using a Noran-OZ confocal laser scanning microscope (OZ CLSM) system. For time-resolved imaging, at t=20 sec, the sample buffer was exchanged by superfusion with buffer containing 10 μM 4, 4-difluoro-5-methyl-4-bora-3a, 4a-diaza-s-indacene-3-dodecanoic acid (C1-BODIPY $C_{12}$) in PBS followed by superfusion with 1 ml of 50 μM BSA in PBS followed by superfusion with PBS alone. Using an excitation wavelength of 480 nm, fluorescence emissions were collected using a 500 Lp band pass filter. Transport of C1-BODIPY $C_{12}$ was monitored (by collection of 200 images) over a 360 sec period beginning 20 sec prior to the addition of the fluorescent ligand. Data were analyzed using InterVision 2D analysis software.

Fatty Acid Transport

Rates of fatty acid transport were determined using a modification of the procedure described by Knoll et al. (1995) *J. Biol. Chem.*, 270, 10861–10867. Cells were grown in YNBD containing the appropriate supplements at 30° C. to mid-log phase ($A_{600}$=1.0), collected by centrifugation, washed once in phosphate buffered saline (PBS) and resuspended in 1/10of the original volume in PBS. 500 µl of cells ($1 \times 10^8$ cells) were preincubated for 10 minutes at 30° C. in PBS and the assay was initiated by the addition of [8-$^3$H] octanoate, [9,10-$^3$H]myristate, [9, 10-$^3$H]oleate, [5, 6, 8, 9, 11, 12, 14, 15-$^3$H] arachidonate at the fatty acid:BSA ratios indicated in the figure legends. At the defined time points (0, 2, 4, and 8 minutes), 100 µl duplicate samples were diluted into 5 ml of PBS containing 0.5% Brij 58 (PBS-Brij) and then were immediately filtered through a Whatman Gf/B-filter. The filters were washed 3 times with PBS-Brij. The uptake reactions were linear between 0 and 5 to 7 minutes following the initiation of the reaction. Rates were defined within the linear range. All wash steps were carried out at room temperature. Filters were air-dried and the amount of cell-associated radioactivity was subsequently determined by scintillation counting. Background counts, less than 1% of the total fatty acid, estimated as the amount of radioactivity on control filters in the absence of cells, were subtracted from the experimental samples. The final data were expressed in pmol fatty acid cell associated fatty acid/minute/$1 \times 10^8$ cells and analyzed using EnzymeKinetics software (v 1.0.4; Trinity Software). All data presented represents the mean (±stand error of the mean) from at least four independent experiments.

Fatty Acyl-CoA Analysis

Cells were grown overnight in YNBD supplemented with amino acids as required and diluted to an $OD_{600}$ of 0.1 in 100 ml YNBD. When the cell density reached an $OD_{600}$ of 0.8, oleic acid was added to a final concentration of 100 µM and cells were grown for the times indicated in the figure legends. Cell growth and metabolism were stopped by addition of 1/10 volume of 6.6 M perchloric acid. Cells were harvested by centrifugation for 10 min at 5000 ×g (4° C.). The pellet was resuspended in 10 mM perchloric acid and the sample was transferred to a 15 ml glass tube. Acid washed cells were again pelleted by centrifugation and the supernatant removed by aspiration. To monitor recovery of fatty acids and fatty acyl-CoA, 100 µg pentanoic acid (in hexane) and 100 µl of 10 µM heptadecanoyl-CoA (dissolved in 1 mg/ml Acyl-CoA Binding Protein (ACBP), 100 mM MES pH 6.0) were added. The total volume was adjusted to 0.8 ml by addition of $H_2O$ and then 3 ml chloroform/methanol (2:1) was added. To facilitate cell breakage, glass beads (2 g, 425–600 µm) were added and the mixture was vigorously shaken for 1 h at 4° C. Cell breakage was confirmed by microscopy. Subsequently, 1 ml of chloroform and 1 ml of $H_2O$ were each added. The samples were vortexed for 30 sec and centrifuged for 10 min at 1500×(4° C.). The upper aqueous phase was discarded; the lower organic phase was gently transferred to a dram glass and used for fatty acid and complex lipid analysis, while the interphase (containing the acyl-CoA esters) was dried under nitrogen. Recombinant $His_6$-bovine ACBP (0.5 mg) in 0.8 ml 100 mM MES-buffer, pH 6.0 was added to the dried fraction and the acyl-CoA esters extracted by shaking for 1 h at 4° C. The suspension was centrifuged for 10 min at 1500×g (4° C.). The supernatant was analyzed by high performance liquid chromatography essentially as described by Schjerling et al. (1996 *J. Biol. Chem.*, 271, 22514–22521) to identify and quantify acyl-CoA species. Acyl-CoA species were identified by comparison of retention times to those of standards.

Free Fatty Acid and Complex Lipid Analyses

The lower organic phase, obtained as described above, was dried under nitrogen, resuspended in 0.1 ml chloroform/methanol (2:1) and divided into two parts. One half was used for total fatty acid analysis. This sample was dried under $N_2$ and resuspended in 0.5 ml NaOH in methanol (20 g/l) and incubated at 100° C. overnight under nitrogen to hydrolyze the acyl esters of natural lipids and to form the methyl esters. The next day, 0.5 ml $BF_3$ (20%) was added and the sample was incubated for 1 h at 100° C. under nitrogen. The fatty acid methyl esters were extracted twice with 0.5 ml hexane. The hexane phases were combined and dried under nitrogen. The methyl esters in the dried sample were analyzed as described in Schjerling et al. 1996 *J. Biol. Chem.*, 271, 22514–22521.

Cellular lipids in the second half of the sample were separated by HPTLC in (hexane:ether:methanol:acetic acids; 90:20:3:2). Lipids were identified corresponding to lipid standards in an iodine-chamber, scraped off and resuspended in chloroform/methanol (2: 1). To monitor recovery, 30 µg pentanoic acid in hexane was added to each fraction except the free fatty acid fraction and the sample was then transferred to a dram glass, dried under $N_2$ and prepared for GC analysis of fatty acids as described above.

Analysis of Acyl CoA Synthetase Activities

Cells were grown to 1.0 $OD_{600}$, harvested by centrifugation, washed twice with PBS, and resuspended to a density of $1.2 \times 10^9$ cells/ml in 200 mM Tris-HCl, pH 8.0, 4 mM EDTA, 5 mM 2-mercaptoethanol, 10% glycerol, 0.1% Triton X-100, 0.5 mM phenylmethylsulfonyl fluoride, 4 µM Pepstatin A and 8 µM Leupeptin. The cells were used by vigorously vortexing the cell suspension containing glass beads for 1 min, 5 times at 0° C. Samples were centrifuged 1500×g for 5 min and supernatants were used to assess acyl-CoA activities. Acyl-CoA synthetase activities were determined in cell extracts as described. See, Black et al. *J. Biol. Chem.*, 272, 4896–903. The reaction mixtures contained 200 mM Tris HCl, pH 7.5, 2.5 mM ATP, 8 mM $MgCl_2$, 2 mM EDTA, 20 mM NaF, 0.1% Triton X-100, fatty acid dissolved in 10 mg/ml α-dextrin (final concentration 50 µM [$^3$H]-decanoate, 50 µM [$^3$H]-oleate, or 10 µM [$^3$H]-lignocerate) 0.5mM coenzymeA, and cell extract in a total volume of 0.5 ml. The reactions were initiated by the addition of coenzymeA, incubated at 30° C. for 20 min, and terminated by the addition of 2.5 ml isopropanol:n-heptane: 1M $H_2SO_4$ (40:10:1). The radioactive fatty acid was removed by organic extraction using n-heptane. Acyl-CoA formed during the reaction remained in the aqueous fraction and was quantified by scintillation counting. Protein concentrations in the enzyme extracts and purified enzyme samples were determined using the Bradford assay and bovine serum albumin as, a standard. See, Bradford (1976) *Anal. Biochem.*, 72, 248–254. The values presented represent the average from at least three independent experiments. All experiments were analyzed by analysis of variance using PRIZM software (GraphPad Software, Inc.).

In vivo β-oxidation

From an overnight in YNBD strains of interest were diluted in YNBD to an $OD_{600}$ of 0.05, grown to an $OD_{600}$ of 0.6 and harvested by centrifugation. The cell pellets were washed twice in YP-medium consisting of 0.3% yeast extract, 0.5% peptone, 0.5% potassium phosphate (pH 6.0), and resuspended to a final $OD_{600}$ of 0.6 in YP-medium supplemented with 0.2% oleate, 1% Brij 58, 0.5% potassium phosphate for 15 hours to allow induction of peroxisomes. Cells were then harvested by centrifugation, washed once in PBS containing 1% Brij 58, twice in PBS, and finally resuspended to an $OD_{600}$ of 2.5 in PBS. For assay, aliquots of 200 μl of cell suspension were added to a 25 ml reaction vessel fitted with a center well (Kontes). To initiate the reaction [1-$^{14}$C]oleic acid or [1-$^{14}$C]decanoate were added from an ethanolic stock to a final concentration of 10 μM. Final volumes were 2 ml per reaction in PBS. Reactions were continued for 30 minutes at 30° C. and were terminated by the addition of $H_2SO_4$ to 1N added directly to the cell sample. Radiolabeled $CO_2$ vias trapped for 60 minutes in 50% ethanolamine in ethanol in the center well. Radioactivity trapped in the well was quantified by liquid scintillation counting. The final data were expressed in pmoles per mg protein per min and analyzed using EnzymeKinetics software (v 1.0.4; Trinity Software). Data presented represents the mean (±stand error of the mean) from at least three independent experiments.

Membrane Fluidity

Strains of interest were inoculated from plate stocks to liquid YPD and grown until saturated, generally overnight. The cells were then diluted in fresh media to 0.05 $OD_{600}$ in the media of interest and grown to mid-log phase unless otherwise indicated. Cells were harvested by centrifugation at room temperature, rinsed twice in 10 mM sodium phosphate, pH 7.0 and resuspended to a final concentration of 0.2 $OD_{600}$ in the same buffer. Labeling with diphenylhexatriene (DPH), determination of anisotropy and fluidity values were determined essentially as described by Swan and Watson (1997 Can. J. Microbiol. 43: 70–77). DPH dissolved in tetrahydrofuran was added to a final concentration of 1 μM. Each sample (final volume of 3 ml) was assayed in triplicate. The cells and label were incubated at least 30 minutes prior to determining anisotropy values. Anisotropy was measured in a Perkin Elmer LS50B luminescence spectrometer equipped with polarizing filters using software supplied by the manufacturer. Excitation was at 360 nm and emission at 430 nm. At least four anisotropy measurements were taken over a ten minute period for each sample at each temperature reported.

Materials

Yeast extract, yeast peptone, and yeast nitrogen base were obtained from Difco. Oleic acid and cerulenin were obtained from Sigma. [$^3$H]- or [$^{14}$C]-labeled fatty acids were from DuPont NEN and from American Radiolabeled Chemicals. 4, 4-difluoro-5-methyl-4-bora-3a, 4a-diaza-s-indacene-3-dodecanoic acid (C1-BODIPY $C_{12}$) and diphenylhexatriene (DPH) were purchased from Molecular Probes. DNA oligonucleotides were obtained from Life Technologies. Enzymes required for all DNA manipulations were from Promega, New England Biolabs, U.S. Biochemical Corp., Invitrogen, Perkin-Elmer, or Boehringer Mannheim. All other chemicals were obtained from standard suppliers and were of reagent grade.

Results

Expression of the Mammalian Fatty Acid Transport Protein in S. cerevisiae

Figure 1:
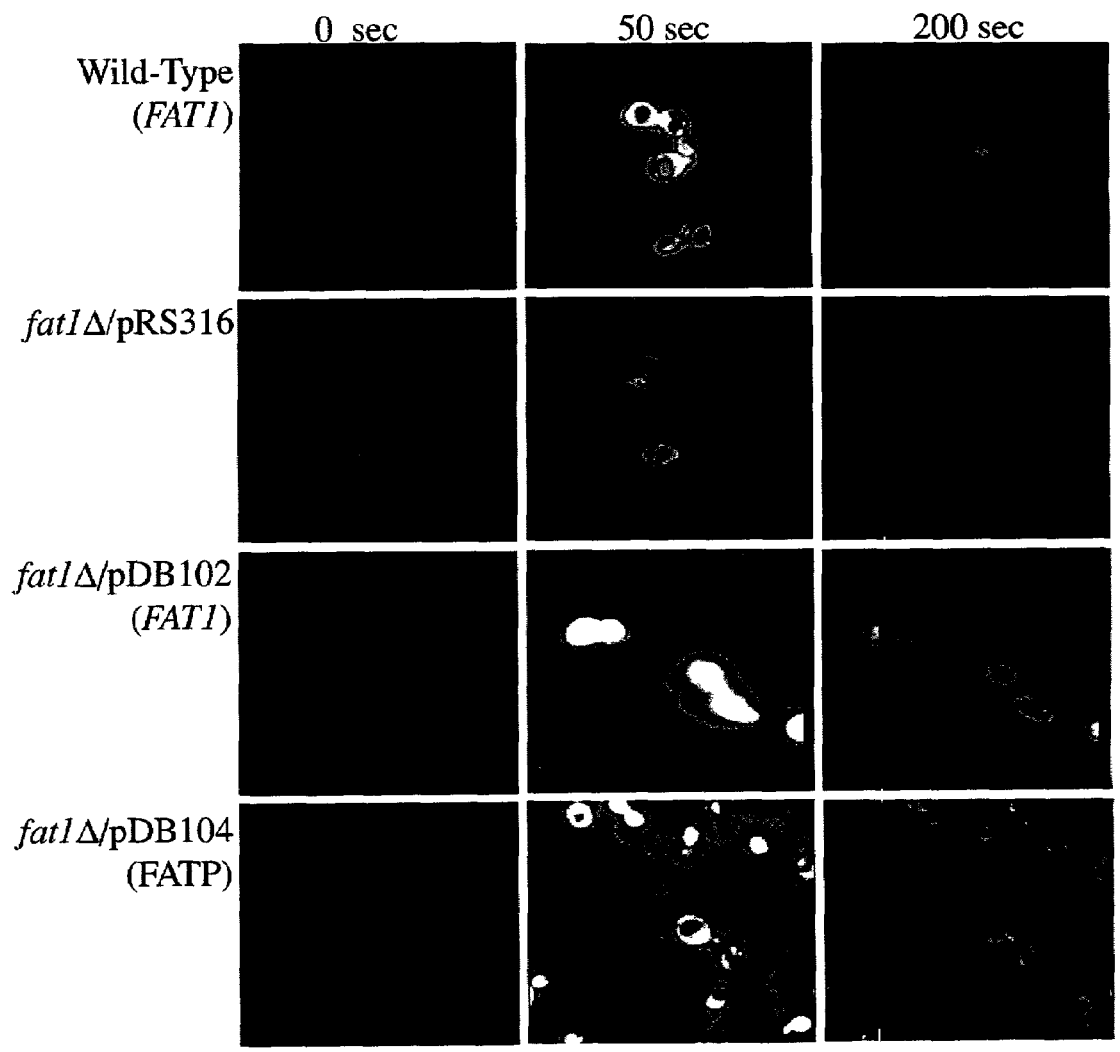
FIG. 1. Fatty acid uptake is restored to fat1Δ strains by cloned yeast Fat1p or murine FATP. Uptake of C1-BODIPY-$C_{12}$ in wild-type and fat1Δ strains transformed with pRS316 (vector control), pDB102 (yeast FAT1) and pDB104 (murine FATP) was monitored using time-lapse confocal fluorescence microscopy. Cells were immobilized on a polylysine-coated slide and perfused with 10 μM C1-BODIPY-$C_{12}$ followed by PBS-BSA and PBS washes as detailed in Example 1. Images gathered at t=0, upon addition of fluorophore, and 50 or 200 sec after wash with PBS containing BSA are shown.

The DNA encoding murine FATP was subcloned from p FATP into the yeast expression vector YpBB358 to give pDB104. The expression of FATP in pDB104 is driven by the constitutive S. cerevisiae glyceraldehyde 3-phosphate dehydrogenase (GPD) gene promoter. The plasmids pRS316 (vector control), pDB102 encoding yeast Fat1p under the control of the native FAT1 promoter and pDB104 (FATP+) were each transfected into the fat1Δ strain. Transfectants were preliminarily analyzed by evaluating the patterns of long-chain fatty acid uptake using the fluorophore-labeled long-chain fatty acid analog, 4, 4-difluoro-5-methyl-4-bora-3a, 4a-diaza-s-indacene-3-dodecanoic acid (C1-BODIPY $C_{12}$). Wild-type cells accumulate this fluorescent analogue and that the compound remains cell-associated when cells are extensively washed with a solution containing the fatty acid binding protein bovine serum albumin (BSA). In contrast, cells with a deletion in FAT1 (fat1Δ) fail to accumulate the fluorescent compound. FIG. 1 shows that transformants of the fat1Δ strain carrying either pDB102 encoding yeast Fat1p or pDB104 encoding murine FATP accumulated C1-BODIPY $C_{12}$ at levels comparable to the wild-type strain. Presentation of the fluorophore and removal occurred rapidly (within one minute) using a flow cell and the compound could not be removed from cells expressing Fat1p or FATP by extensive washing with BSA. These results indicated that the fluorescent fatty acid analogue is imported into the cell by a process that is dependent upon Fat1p and that import is essentially irreversible. Additionally these results demonstrated that the murine FATP substituted for the native yeast protein in the import process.

Figure 2:
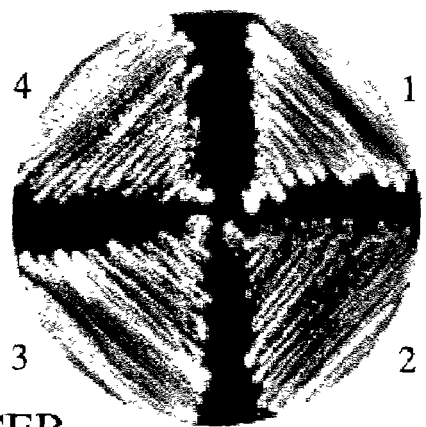
FIGS. 2A, 2B and 2C. Growth is restored to fat1Δ strains by Fat1p or FATP when fatty acid synthase is inactive. Phenotypes of wild-type ("1") and fat1Δ strains transformed with pDB104 (murine FATP) ("2"), pDB102 (yeast fAT1)
Figure 2:
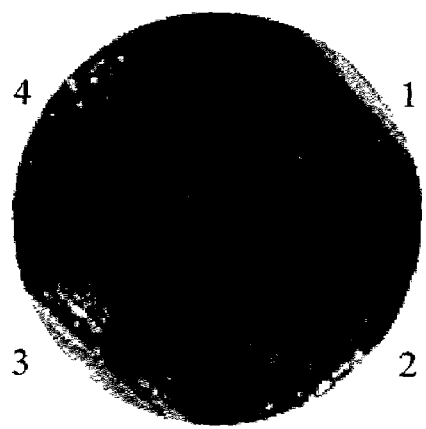
Figure 2:
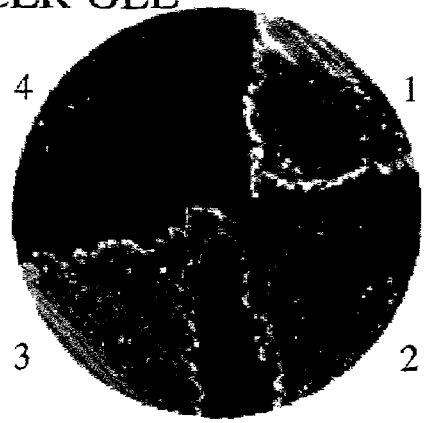

FATP and Fat1p each restore growth of fat1Δ cells when fatty acid synthesis is compromised. The antimicrobial agent cerulenin inhibits yeast fatty acid synthase and renders the cells functionally auxotrophic for fatty acids. The growth of wild-type cells can be rescued by the inclusion of as little as 10 μM long-chain fatty acid in the cerulenin containing media. In contrast, fat1D strains are not rescued by the addition of fatty acids up to 500 μM. As shown in FIG. 2, either the clone encoding yeast Fat1p or that which encodes murine FATP was able to complement the fat1Δ strain grown on YPD plates containing cerulenin and oleate (YPD-CER-OLE) both at 30° C. and 37° C. The transformants of pDB104 encoding the murine protein grew better on YPD-CER-OLE at 37° C. as opposed to 30° C. Others have observed a similar temperature dependence in the complementation patterns of the rat fatty acyl CoA synthetase cDNA cloned into the same expression vector and transformed into a faa1Δ faa2Δ faa3Δ faa4Δ strain. These results may reflect the temperature optimum for the mammalian enzymes.

Figure 3:
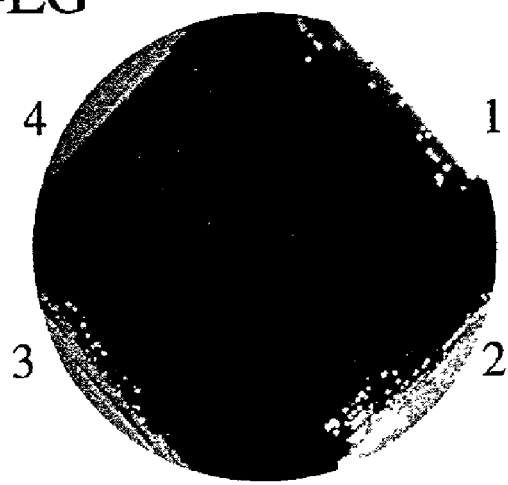
Figure 3:
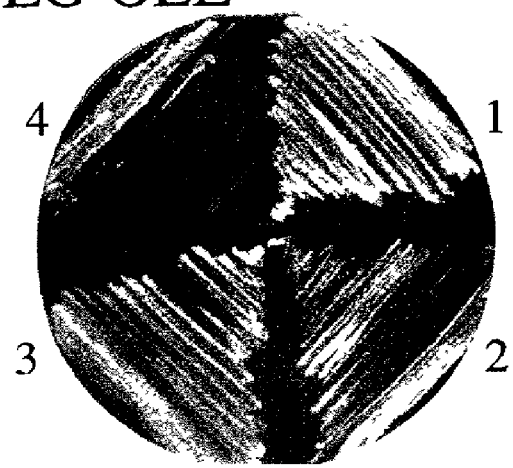

S. cerevisiae has a single fatty acid desaturase encoded within the OLE1 gene, which is essential for growth. This enzyme requires oxygen for catalysis and is non-functional when yeast are grown anaerobically. We therefore hypothesized that the putative fatty acid transport protein Fat1p would also be essential under these growth conditions when yeast are dependent upon long-chain unsaturated fatty acids from an exogenous source. To test this, cells were grown on YNBD containing ergosterol (YNBDE) or YNBDE containing 100 μM oleate (YNBDEO) at 30° C. in an anaerobic chamber (FIG. 3). Consistent with this, the fat1Δ strain was unable to grow even when the media was supplemented with oleate. Expression from an episome of either Fat1p or FATP into the fat1Δ strain restored growth to wild-type levels.

Levels of long-chain fatty acid transport are restored in fat1Δ strains transformed with either pDB102 (FAT1) or pDB104 (FATP). On the basis of the data presented above, both Fat1p and FATP appeared to carryout the same biochemical function, which contributes to the transport of exogenous long-chain fatty acids into the cell. In order to more fully quantify and define the role of Fat1p and FATP in the transport of long-chain fatty acids, uptake assays were performed in the wild-type,fat1Δ,fat1Δ/pDB102 (encoding Fat1p), fat1Δ/pDB104 (encoding FATP) strains using octaonoate (C8:0), myristate (C14:0), oleate (C18:1) and arachidonate (C20:4) as substrates. In these experiments, the fatty acid substrates were provided to the cell at low, physiologically relevant, concentrations. The molar ratios of bovine serum albumin (BSA) to fatty acid were adjusted to give free fatty acid concentrations of 60 nM, 125 nM or 400 nM as described by Spector, et al. (1971) *Biochemistry*, 10, 3229–3232. As illustrated in FIG. 4A, no differences were observed in the rates of octanoate transport between the four strains. However, as the chain-length of the fatty acid was increased, differences become more apparent (FIG. 4B–4D). At all three fatty acid concentrations the rates of transport of C14:0, C18:1 and C20:4 defined for the fat1Δ strain were 2- to 3-fold reduced when compared to the wild-type. The long-chain fatty acid transport defect was restored to wild-type levels in the fat1Δ strain transformed with either pDB102 (encoding yeast Fat1p) or pDB104 (encoding murine FATP). These data concur with the data presented above to support the conclusion that fatty acid import from an exogenous source is compromised in cells deficient in FAT1. Importantly, yeast Fat1p and murine FATP appear to be functionally equivalent in the uptake of exogenous long-chain fatty acids. The specificity of this transport system appears to be toward long-chain fatty acids (C14:0 to C20:4) as there were no apparent differences in transport using octanoate, a medium-chain fatty acid substrate.

Deletion of FAT1 alters metabolism of imported fatty acids. On the basis of the data presented above, we hypothesized that Fat1p is a key player in fatty acid import and cellular utilization of long-chain fatty acids. Therefore, deletion of FAT1 should result in alterations in the patterns of fatty acid activation, incorporation of imported fatty acids into complex lipids and subsequent degradation by β-oxidation.

We first evaluated the ability of yeast strains to β-oxidize long-chain fatty acids. A reduction in β-oxidation could be due to decreased fatty acid import, decreased activation of fatty acids to the CoA thioester, and/or reduced ability to induce peroxisomes and the β-oxidation enzymes. Therefore, we expected that fat1Δ cells, which have an apparent block in fatty acid import, would β-oxidize fatty acids to a limited extent. This was confirmed by the data in FIG. 5 that show β-oxidation of C18:1 was reduced to 30% wild-type levels in fat1Δ strains. By comparison, fat1Δ strains transformed with either pDB102 (Fat1p) or pDB104 (murine FATP) had levels of β-oxidation that were equivalent to the wild-type strain.

We next evaluated acyl-CoA pools to determine if a deficiency in Fat1p could be attributed to an inability, or a decreased ability to synthesize activated substrates for complex lipid synthesis or fatty acid degradation. The levels of long-chain acyl-CoA from cells grown in YNBD were essentially equivalent between the wild-type and mutant strain (FIG. 6). We also compared oleoyl-CoA pools between cells grown with or without exogenously supplied fatty acids to estimate the amount contributed by endogenous synthesis (YNBD grown cells) and the amount contributed from an exogenous source (YNBD with oleate). For these experiments, the wild-type, fat1Δ, and fat1Δ containing either pDB102 or pDB104 cells were grown to mid-log phase in YNBD then 100 μM oleate was added. Samples were removed for acyl-CoA analysis at 0, 30 and 60 min. after the addition of oleate. The data presented in FIG. 6 showed that the intracellular pools of oleoyl-CoA were similar between the strains prior to the addition of oleate. Oleoyl-CoA levels increased 4- to 5-fold upon addition of oleate to the culture media of wild-type cells or cells transformed with complementing clones. By comparison, levels increased less than 1.5-fold in the fat1Δ strain. Oleoyl-CoA synthetase activities in wild-type and the fat1Δ strains were essentially unchanged. Therefore the reduced levels of oleoyl-CoA in the fat1Δ strain grown in oleate are not the consequence of depressed levels of acyl-CoA synthetase activity but rather are more likely to be due to more limited substrate. Current evidence indicates that in *S. cerevisiae* the synthesis of long chain acyl-CoA from an exogenous source is the function of Faa1p during log phase growth and Faa4p during stationary phase.

Alterations in very long chain free fatty acids associated with mutations in FAT1 do not alter membrane fluidity. Recent reports indicate that strains carrying mutations in FAT1 had elevated levels of very long-chain fatty acids and decreased levels of VLACS activity. Given no difference between wild-type and fat1Δ strains in long-chain ACS activities using C14:0, C16:0 or C18:1 as substrates, we also assessed ACS activity in cell extracts using lignoceric acid (C24:0) as substrate (FIG. 7). We found lignoceryl-CoA synthetase activity was moderately reduced (approximately 40%) in the fat1Δ strain. Introduction of FATP or Fat1p restored activities but it appeared that Fat1p was more efficient compared to FATP. This may have been due to the fact that the assay was preformed at 30° C. (the preferred growth temperature for yeast) rather than 37° C. (the preferred temperature for mammalian cells). In contrast, when VLACS activity was measured in extracts from cells grown in media supplemented with oleate, no significant differences were found between wild-type and the fat1Δ strain or the fat1Δ strain transformed with pDB102 or pDB104 (FIG. 7). It is important to note that VLACS activity is a minor component (app. 1%) of the total cellular ACS activity and deletion of FAT1 reduces but does not eliminate VLACS activity (FIG. 7).

The methods used to estimate VLCFA levels in the previous, studies did not distinguish between free pools of VLCFA and VLCFA incorporated into complex lipids. Therefore, we separated the free fatty acids from the complex lipids prior to analysis. As shown in FIG. 8A and 8B, the fatty acid composition of the complex lipids are, to the limits of the sensitivity of the assay system, unchanged and the elevated levels of VLCFA can be attributed to the free fatty acid pool.

The data reported above led us to question whether the phenotypes associated with deletion of FAT1, particularly with regards to fatty acid transport, were due to alterations in membrane fluidity caused by elevated levels of very long-chain fatty acids. It has been noted that alterations in membrane fluidity cause pleiotropic effects on membrane-associated functions including transport, respiration and DNA replication. In *S. cerevisiae*, alterations in fluidity occur during stress response and in stationary phase. To estimate membrane fluidity, anisotropy measurements were made on whole cells treated with the fluorescent fatty acid analogue diphenylhexatriene (DPH). DPH is a well characterized and efficient probe routinely used to evaluate changes in fluidity. As shown in Table 5, differences in fluidity were observed for cells assessed during log phase growth (i. e. <1.0 $OD_{600}$) by comparison to late log phase (i. e. >2.0 $OD_{600}$) and differencess were observed for cells grown in rich media, YPD, compared with minimal media, YNBD. However, there were no differences observed between the wild-type parent and the fat1Δ derivative under any growth condition tested. Alterations in apparent fluidity that occurred when the temperature at which anisotropy was measured were changed were also similar between the two strains (FIG. 9). Therefore alterations in fatty acid transport attributed to FAT1 are not merely due to changes in membrane fluidity.

Localization of Fat1p Using GFP-Fat1p

Figure 10:
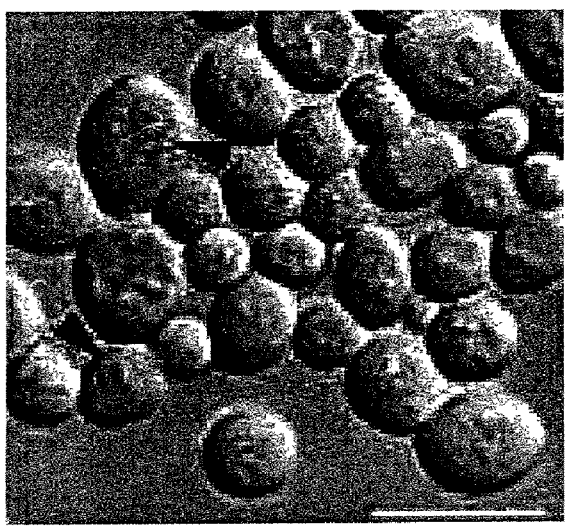
Figure 10:
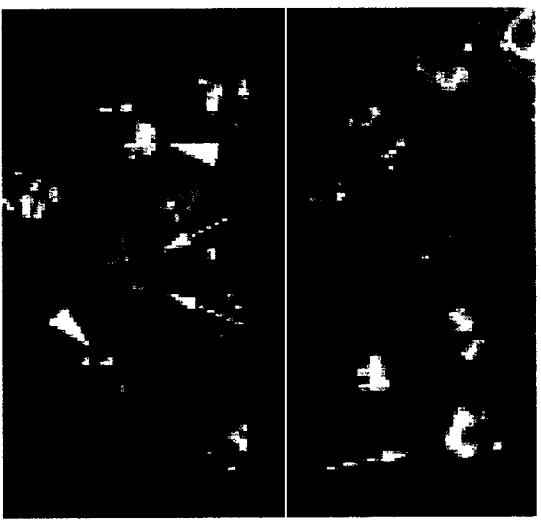

On the basis of our past work on Fat1p and the data described above, we presumed that Fat1p would be associated with the plasma membrane as a component of a fatty acid transport apparatus. In order to define the localization of Fat1p, we chose to employ the amino-terminal green fluorescent vector pUG36 (developed by Niedenthal et al. (1996) *Yeast* 12: 773–786) to generate a GFP-FAT1 fusion (pDB220). Both pUG36 (GFP control) or pDB302 (GFP-FAT1) were transformed into W303a Ade$^+$ and localization monitored using confocal laser scanning microscopy (FIG. 10). As shown in FIG. 10B, GFP-Fat1p localizes at the periphery as expected for the plasma membrane, but is also found concentrated towards the poles of the cell. The nature of this concentrated localization is unknown, but may correspond to regions of bud formation, lipid bodies and/or sites of high lipid turnover. There is also some internal labeling, which may correspond to localization within the endoplasmic reticulum.

Discussion

Fat1p and FATP are Functional Equivalents

In previous work, we identified *S. cerevisiae* Fat1p (also known by the *S. cerevisiae* genome designation YBR041w) and demonstrated that deletion of the gene FAT1 results in a number of growth and biochemical phenotypes consistent with the hypothesis that Fat1p functions in fatty acid import. See, Færgeman et al. (1997) *J. Biol. Chem.* 272: 8531–8538. We demonstrate here that yeast Fat1p and murine FATP are functionally equivalent. Strains that are deleted for FAT1 have at least five phenotypes expected of cells with restricted ability to import fatty acids. These mutant cells fail to grow on media containing the fatty acid synthesis inhibitor cerulenin even when the long-chain fatty acid oleate was supplied in the growth media. Nor do cells grow when cultured under hypoxic conditions when cells are auxotrophic for unsaturated fatty acids. Mutant cells fail to accumulate the fluorescent long-chain fatty acid fatty acid analogue C1-BODIPY-C$_{12}$ and have a greatly diminished capacity to transport exogenous long-chain fatty acids. Utilization of fatty acids, in β-oxidation is also diminished in mutant cells by comparison with wild-type. Each of these phenotypes are eliminated when the mutant strains are transformed with either a clone encoding the yeast Fat1p or an expression clone encoding the murine FATP. Therefore, yeast Fat1p and murine FATP are functional orthologues.

Fat1p is Required for Fatty Acid Import in *S. cerevisiae*

It is extremely difficult to dissociate fatty acid transport from metabolic utilization. In yeast and higher eukaryotes, one mechanism promoting fatty acid transport involves the coupling of transport with activation to CoA thioesters. The concomitant transport and activation result in activated fatty acids, which are metabolized very quickly. This is clearly the case in the bacterial paradigm. We have established that in *Escherichia coli*, the outer membrane-bound fatty acid transport protein FadL and the inner membrane associated fatty acyl-CoA synthetase FadD function in concert in to promote fatty acid transport by a process termed vectorial acylation. See, DiRusso & Black (1999) *Mol. Cell. Biochem.*, 192, 41–52; Black et al. (1987) *J. Biol. Chem.*, 262, 1412–1419; Black (1990) *Biochim. Biophys. Acta.* 1046, 97–105. Cells carrying a deletion in the genes encoding either FadL (fadL) or FadD (fadD) are unable to transport exogenous long chain fatty acids. See, Black et al. (1997) *J. Biol. Chem.*, 272, 4896–903; Black & Zhang (1995) *Biochem. J.*, 310, 389–394; Kumar & Black (1991) *J. Biol. Chem.*, 266, 1348–1353; Kumar & Black (199)3 *J. Biol. Chem.*, 268, 15469–15476. FadL-specific fatty acid binding is distinguishable from transport in certain altered fadL alleles (See, Black & Zhang (1995) *Biochem. J.*, 310, 389–394; Kumar & Black (1991) *J. Biol. Chem.*, 266, 1348–1353; Kumar & Black (1993) *J. Biol. Chem.*, 268, 15469–15476) and when the cells carry mutations in fadD (See, Black (1990) *Biochim. Biophys. Acta.* 1046, 97–105). In the context of transport, the inner membrane-associated fatty acyl CoA synthetase of *E. coli* is proposed to function by abstracting fatty acids from the membrane with the concomitant production of fatty acyl CoA. See, Azizan et al. (1999) *Arch. Biochem. Biophys,* 365, 299–306.

In yeast and higher eukaryotes the same fundamental process is likely to be operational. We have recently shown that in addition to Fat1p, an acyl-CoA synthetase encoded within yeast FAA1 or FAA4 (Faa1p or Faa4p respectively) are required for efficient fatty acid import. Similarly, when the clone encoding murine FATP was selected using a functional assay to screen expression libraries, a distinct fatty acyl-CoA synthetase was also identified. See, Schaffer & Lodish (1994) *Cell*, 79, 427–436. Furthermore, in the murine model the fatty acyl-CoA synthetase ACS1 and FATP co-localize to the plasma membrane and potentiate fatty acid import. As shown in here, Fat1p also is localized to the plasma membrane. We propose that Fat1p like FATP functions in concert with the fatty acyl CoA synthetases to potentiate the coupled transport and activation of exogenous long-chain fatty acids. Upon thioesterification with coenzyme A the fatty acyl-CoA is channeled to sites of metabolic utilization including membrane synthesis and peroxisomal β-oxidation.

There are distinct differences as well as similarities between the bacterial fatty acid import system and that of envisioned for yeast. The fatty acid transport protein FadL resides in the outer membrane and is proposed to form a β-barrel specific for long-chain fatty acids. See, Cristalli et al. (2000) *Arch. Biochem. Biophys.*, 377: 324–333. FadL has no homology to Fat1p or other members of the AMP forming family of proteins, which includes the fatty acyl-CoA synthetases. No Fat1p homologue has been identified in *E. coli*. See, Azizan & Black (1994) *J. Bacteriol.*, 176, 6653–6662. The role of fatty acyl CoA synthetase in fatty acid transport in both bacteria and yeast appears to be comparable: Esterification of exogenous long-chain fatty acids concomitant with transport. The phenotypic defect in long-chain fatty acid transport observed in yeast fat1Δ mutant cells is masked under high fatty acid (>1 mM) growth conditions. By contrast, *E. coli* strains carrying deletions in either fadL or fadD, do not transport long-chain fatty acids even when provided in the growth media at very high concentrations (>5 mM). Despite these differences, our data support the conclusion that Fat1p is required for maximal fatty acid transport. We propose that in the natural habitat when oxygen is limiting and fatty acid desaturase inactive, FATP is an essential protein. This conclusion is verified by results shown in Table 1.

TABLE 1

Comparison of membrane fluidity of wild-type and fat1Δ Strains

| Strain | Growth Condition | Anisotropy "r" | Fluidity "Log 1/r" |
|---|---|---|---|
| W303a | YPD to 0.881 OD$_{600}$ | 0.176 | 0.754 |
| W303a fat1Δ | YPD to 0.978 OD$_{600}$ | 0.197 | 0.706 |
| W303a | YPD to 2.071 OD$_{600}$ | 0.208 | 0.682 |
| W303a fat1Δ | YPD to 2.065 OD$_{600}$ | 0.201 | 0.697 |
| W303a | YNBD to 0.479 OD$_{600}$ | 0.147 | 0.833 |
| W303a fat1Δ | YNBD to 0.149 OD$_{600}$ | 0.139 | 0.857 |

Anisotropy was measured using 100 nM DPH and cells at 0.1–0.2 OD$_{600}$ at 25° C.

Example 2

Exogenous long-chain fatty acids are activated to coenzymeA derivatives prior to metabolic utilization. In the yeast *Saccharomyces cerevisiae* the activation of these compounds prior to metabolic utilization proceeds through the fatty acyl-CoA synthetases Faa1p and Faa4p. Faa1p or Faa4p are essential for long-chain fatty acid import suggesting that one or both of these enzymes are components of the fatty acid transport system, which also includes Fat1p. By monitoring the intracellular accumulation of the fluorescent long-chain fatty acid analogue C1-BODIPY-C$_{12}$, long-chain fatty acid transport was shown to be severely restricted in a faa1Δ faa4Δ strain. These data established for the first time a mechanistic linkage between the import and activation of exogenous fatty acids in yeast.

Import of fatty acids into yeast is an essential function when cells are auxotrophic for fatty acids. This occurs in the natural environment when oxygen is limiting due to inhibition of the O$_2$-requiring Δ$^9$-acyl-CoA desaturase (encoded by OLE1). In addition, a conditional auxotrophy is imposed when cells are cultured in media containing the fatty acid synthase inhibitor cerulenin. In yeast, fatty acid import is saturable and dependent upon Fat1p, an ortholog of the murine fatty acid transport protein, FATP. Fat1p is one member of a multi-component fatty acid import apparatus. In the well characterized *E coli* model system, fatty acid import is not only dependent upon the outer membrane-bound transporter, FadL, but also requires the fatty acyl-CoA synthetase, FadD. In this regard, long-chain fatty acid transport is described as vectorial acylation. Since in eukaryotic systems, imported fatty acids must, likewise, be activated by esterification to coenzyme A prior to metabolic utilization, a similar coupling of fatty acid import and activation is one mechanism that drives this process.

In *S. cerevisiae*, four fatty acyl-CoA synthetases encoded by separate genes have been identified: Faa1p, Faa2p, Faa3p, and Faa4p. Cells carrying deletions in each of the four FAA genes are viable suggesting de novo fatty acid synthesis provides sufficient acyl-CoA for essential cellular functions. Faa1p and Faa4p are the primary enzymes involved in activation of imported long-chain fatty acids (C$_{12}$–C$_{18}$), while Faa2p appears to be involved in activation of medium-chain fatty acids directed towards peroxisomal β-oxidation. The physiological role of Faa3p, which is most active toward fatty acids >C$_{18}$, has not yet been defined. More recently, very long-chain (C$_{22}$–C$_{26}$) acyl-CoA synthetase activity has also be(n attributed to Fat1p, which plays a pivotal role in long chain fatty acid import.

The data below support the concept that transport is complex and includes both diffusional and protein mediated components. One of the protein components is Fat1p. A long chain fatty acyl-CoA synthetase, either Faa1p or Faa4p, is also required. In addition, deletion of FAA1 and/or FAA4 alters the endogenous acyl-CoA pools in the absence of exogenous fatty acid, suggesting these enzymes also play a role in intracellular acyl CoA metabolism.

Experimental Methods

Strains, Media and Plasmids

The *Saccharomyces cerevisiae* strains YB332 (a; ura3-52; leu2-3,112; his3Δ-200; ade2-101; lys2-801), YB513 (a; ura3-52; leu2-3,112; his3Δ-200; ade2-101; lys2-01; faa1Δ:: HIS3), YB524 (a; ura3-52; leu2-3,112; his3Δ-200; ade2-101; lys2-801, faa4Δ::LYS2), YB525 (a; ura3-52; leu2-3, 112; his3Δ-200; ade2-101; lys2-801; faa1Δ::HIS3; faa4Δ:: LYS2) and YB526 (a; ura3-52; his3Δ200; ade2-10; lys2-80; leu2-3,112; faa1Δ::HIS3; faa2Δ::LEU2; faa3Δ::LEU;2 faa4Δ::LYS2) were obtained from J. I. Gordon (Washington University of Medicine, St. Louis, Mo., USA) and used in all experiments described. YPDA consisted of 1% yeast extract, 2% peptone, 2% dextrose and 20 mg/L adenine-hemisulfate. Yeast supplemented minimal media contained 0.67% yeast nitrogen base (YNB), 2% dextrose, adenine (20 mg/L), uracil (20 mg/L) and amino acids as required (arginine, tryptophan, methionine, histidine, and tyrosine (20 mg/L); lysine (30 mg/L); and leucine (100 mg/L)). To assess growth when fatty acid synthase was inhibited, cells were grown on YNBD plates supplemented with 45 μM cerulenin and 100 μM oleic acid (YNB-CER-OLE). To assess growth under hypoxic conditions cells were grown on YNBD plates supplemented with 20 μg/ml ergosterol, 100 μM oleic acid, and amino acids and uracil as required (YNB-EG-OLE). Growth in liquid culture and on plates was at 30° C.

The plasmids pGALFAA1 and pGALFAA4 (FAA1 and FAA4 under the control of the GAL7 promoter respectively) were obtained from InvitroGen. Transformation of the faa1Δ faa4Δ strain was accomplished using the high efficiency lithium acetate protocol essentially as described in Chen et al. (1992) *Curr. Genet.* 21, 83–84.

Fatty Acid Uptake

Fatty acid transport was assessed using confocal laser scanning microscopy (CLSM) and the fluorescent long-chain fatty acid analogue 4, 4-difluoro-5-methyl-4-bora-3a, 4a-diaza-s-indacene-3-dodecanoic acid (C1-BODIPY-C$_{12}$) as described in Færgeman et al. (1997) *J. Biol. Chem.* 247: 8531–8538; DiRusso et al. (2000) *Eur. J. Biochem.* 267, 4422–4433.

Cells were grown in YNBD to OD$_{600}$ of 0.8–1.0, harvested by centrifugation, washed twice in phosphate buffered saline (PBS) and were finally resuspended in ¹/₁₀ vol PBS. Cells (faa1Δ faa4Δ) harboring either pGALFAA1 or pGALFAA4 were grown from an overnight culture in YNB containing 4% sucrose to an OD$_{600}$ of 0.4 at which time cultures were split, 2% glucose added to one, 2% galactose added to the other. Growth was continued until the cell density reached an OD$_{600}$ of 0.8. Cells were harvested, washed with PBS and resuspended in ¹/₁₀ vol PBS as detailed above. All steps were performed at room temperature. Washed cells were incubated with 10 μM C1-BODIPY-C$_{12}$ for 60 sec, washed in PBS containing 50 μM fatty acid free BSA (2×), PBS, resuspended in PBS and visualized on an NORAN-OZ CLSM, interfaced with a Nikon Diaphot 200 inverted microscope equipped with a PlanApo 60×, 1.4 NA oil-immersion objective lens. No efflux of fatty acid was found during the time course used during these experimental conditions. The use of C1-BODIPY-C$_{12}$ at a final concentration of 10 μM was chosen as this allowed for the fluorescent signal to b, readily visualized using CLSM. The instrument settings for brightness, contrast, laser power and slit size were optimized for the brightest sample to assure that the CLSM was set for its full dynamic range. The same settings were used for all subsequent image collections.

Quantitative Fatty Acid Uptake Measurements

Rates of fatty acid transport were also determined using the filtration assay previously described in DiRusso et al. (2000) *Eur. J. Biochem.* 267, 4422–4433. Cells were grown in YNBD containing the appropriate supplements at 30° C. to mid-log phase, collected by centrifugation, washed once in phosphate buffered saline (PBS) and resuspended in ⅒ of the original volume in PBS. 500 µl of cells ($1 \times 10^8$ cells) were preincubated for 10 minutes at 30° C. in PBS and the assay was initiated by the addition of [9, 10-$^3$H]oleate at the fatty acid:BSA ratios indicated in the table legend. At the defined time points (0, 2, 4, and 6 minutes), 100 µl duplicate samples were diluted into 5 ml of PBS containing 0.5% Brij 58 (PBS-Brij) and then were immediately filtered through a Whatman Gf/B-filter. The filters were washed 3 times with PBS-Brij. Transport rates were defined within the linear range. No fatty acid efflux was observed over the six-minute period using this experimental approach. All wash steps were carried out at room temperature. Filters were air-dried and radioactivity determined by scintillation counting. The final data were expressed in pmol oleate transported/minute/$1 \times 10^8$ cells and subjected to analysis of variance using PRIZM software (GraphPad Software, Inc.). All data presented represents the mean (±stand error of the mean) from two independent experiments performed in duplicate.

Fatty Acid and Fatty Acyl-CoA Analyses

Total fatty acid profiles were determined in cells grown in YNBD to an $OD_{600}$ of 0.8. Cell growth and metabolism were stopped by addition of ⅒ volume of 6.6 M perchloric acid. Cells were harvested by centrifugation for 10 min at 5,000×g (4° C.). The cell pellets were resuspended in water and 100 µg heptadecanoic acid (in hexane) added as an internal standard. The lipids were extracted using a modification of the technique described by Bligh and Dyer (1959 *Can. J. Biochem. Physiol.* 37: 911–917) using glass beads (2 g/50 ml cultures, 425–600 µm) to break the cells. Following extraction, the lipids were dried under a stream of $N_2$, resuspended in 0.4 ml NaOH in methanol (20 g/L), and incubated overnight at 100° C. $BF_3$ (0.5 ml; 20%) was added and incubation continued for 1 hr at 100° C. The methyl esters were extracted with hexane, dried, resuspended in 1 ml methyl acetate and analyzed by gas chromatography using an HP 225 column. The data are presented in mole % fatty acid and are the mean of at least three independent experiments performed in duplicate.

For fatty acyl-CoA determinations, cells were grown overnight in YPDA and diluted to an $OD_{600}$ of 0.1 in 100 ml YNBD. When the cell density reached cm $OD_{600}$ of 0.8, oleic acid was added to a final concentration of 100 µM and grown for the times indicated in the figure legend. Cell growth and metabolism were stopped by addition of ⅒ volume of 6.6 M perchloric acid. Cells were harvested by centrifugation for 10 min at 5,000×g (4° C.). Acyl-CoA extraction, quantification and identification were performed as described by Schjerling et al. (1996) *J. Biol. Chem.* 271, 22514–22521.

Acyl-CoA Synthetase Activity

Cells were grown from overnight cultures in YPDA and grown to $OD_{600}$ of 1.0. Following growth, cells were harvested by centrifugation, washed twice with PBS, and resuspended to a density of $1.2 \times 10^9$ cells/ml in 200 mM Tris-HCl, pH 8.0, 4 mM EDTA, 5 mM 2-mercaptoethanol, 10% glycerol, 0.01% Triton X-100, 0.5 mM phenylmethylsulfonyl fluoride, 4 µM Pepstatin A and 8 µM Leupeptin. The cells were lysed by vigorously vortexing the cell suspension containing glass beads for 1 min, 5 times at 0° C. Samples were clarified by centrifugation (1,500×g, 5 min) and supernatants were used to assess acyl-CoA activities. Acyl-CoA synthetase activities were determined in cell extracts as described in Black et al. (1997) *J. Biol. Chem.* 272, 4896–4903. The reaction mixtures contained 200 mM Tris HCl, pH 7.5, 2.5 mM ATP, 8 mM $MgCl_2$, 2 mM EDTA, 20 mM NaF, 0.01% Triton X-100, fatty acid dissolved in 10 mg/ml α-dextrin (final concentrations of fatty acids were 50 µM), 0.5 mM coenzymeA, and cell extract in a total volume of 0.5 ml. The reactions were initiated by the addition of coenzymeA, incubated at 30° C. for 20 min, and terminated by the addition of 2.5 ml isopropanol:n-heptane:1M $H_2SO_4$ (40:10:1). The radioactive fatty acid was removed by organic extraction using n-heptane. Acyl-CoA formed during the reaction remained in the aqueous fraction and was quantified by scintillation counting. Protein concentrations in the enzyme extracts and purified enzyme samples were determined using the Bradford assay and bovine serum albumin as a standard. See Bradford (1976) *Anal. Biochem.* 72, 248–254. The values presented represent the average from at least three independent experiments. All experiments were analyzed by analysis of variance using PRIZM software.

In vivo β-oxidation

Cells were grown and peroxisomes induced in YP-medium (0.3% yeast extract, 0.5% peptone, 0.5% potassium phosphate (pH 6.0), 3% glycerol) containing 0.2% oleate and 1% Brij58 (YPO) as described by Rottensteiner et al. (1996) *EMBO J.* 15, 2924–2934. Following induction, cells were harvested by centrifugation, washed once in PBS-Brij58, twice in PBS, and finally resuspended to an $OD_{600}$ of 2.5 in PBS. For assay, aliquots of 200 µl of cell suspension were added to a 25 ml reaction vessel fitted with a center well (Kontes) in a total volume of 2 ml PBS. To initiate the reaction [1-$^{14}$C]oleic acid was added from an ethanolic stock to a final concentration of 10 µM. Reactions were continued for 30 minutes at 30° C. and were terminated by the addition of $H_2SO_4$ to 1 N added directly to the cell sample. Radiolabeled $CO_2$ was trapped for 60 min in 50% ethanolamine in ethanol in the center well. Radioactivity trapped in the well was quantified by liquid scintillation counting. The final data were expressed in pmoles/min/mg protein and analyzed using PRIZM. Data presented represents the mean (±stand error of the mean) from at least three independent experiments.

RNA Isolation and Northern Blot Analyses

Cells were grown from an overnight culture into YPDA to an $OD_{600}$ of 0.1 and grown to an $OD_{600}$ of 0.6. Cells were harvested, washed twice in YP-medium (1% yeast extract, 2% peptone) and diluted to an $OD_{600}$ of 0.05 in YP-medium containing with 2% glucose, 3% glycerol, or 3% glycerol 0.2% oleate, and 1% Brij58 58 and grown to an $OD_{600}$ of 0.6. Cells were harvested by centrifugation at 0° C., washed, RNA extracted and analyzed by Northern blotting. See, Lowry & Zitomer (1984) *Proc. Natl. Acad. Sci. USA* 81: 6129–6133. The hybridization probes (OLE1, POX1, FAA2, and ACT1) used were PCR amplified from yeast genomic DNA, gel purified and $^{32}$P-labeled using [α-$^{32}$P]-dCTP and the Prime-a-Gene kit from Promega.

Materials

Yeast extract, yeast peptone, and yeast nitrogen base were obtained from Difco. Oleic acid was obtained from Sigma. [$^3$H]- or [$^{14}$C]-labeled fatty acids were from DuPont NEN, American Radiochemicals, or Sigma. C1-BODIPY-$C_{12}$ was purchased from Molecular Probes. Enzymes required for all DNA manipulations were from Promega, New England Biolabs, U.S. Biochemical Corp., or Boehringer Mannheim.

Results

Figure 11:
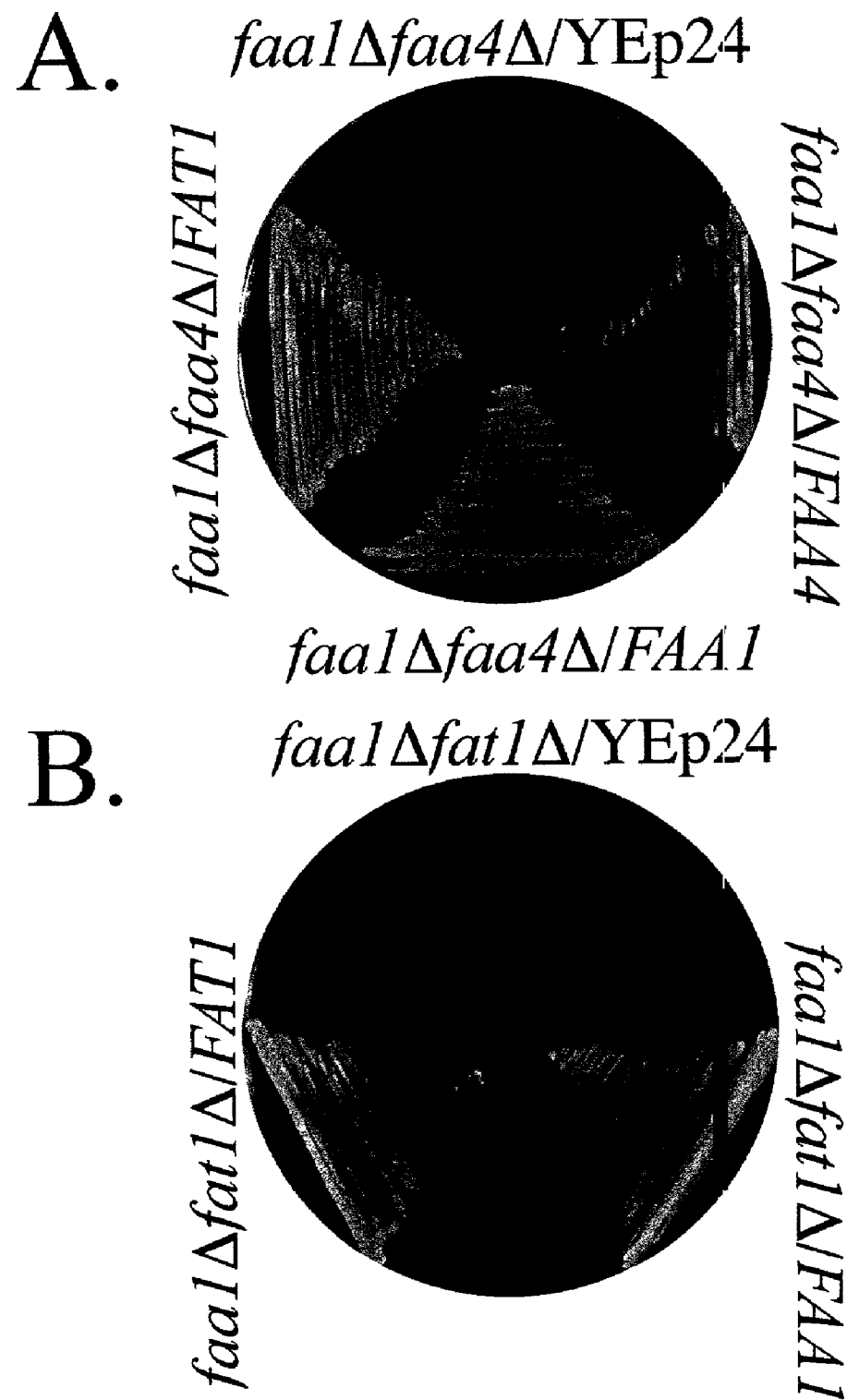

FAA1 and FAA4 are required for growth of fatty acid auxotophs due to deficiencies in both fatty acid import and activation. The *Saccharomyces cerevisiae* fatty acid activating enzyme Faa1p was first identified as a gene required for growth when the fatty acid synthesis inhibitor cerulenin was included in the growth media containing the long-chain saturated fatty acids myristate or palmitate. Subsequently, three additional genes encoding the fatty acyl CoA synthetases Faa2p, Faa3p and Faa4p were identified by sequence comparisons and reverse genetics. Further characterization of the cloned genes and enzymes indicated Faa4p had overlapping functions with Faa1p and either one was sufficient to support growth under these synthetic lethal conditions. In the natural environment, yeast are auxotrophic for long-chain unsaturated fatty acids when growing under hypoxic conditions since the $O_2$-requiring $\Delta^9$-acyl-CoA desaturase necessary for de novo unsaturated fatty acid synthesis is inactive. Deletion of both FAA1 and FAA4 was required to completely eliminate growth under these culture conditions (FIG. 11A). This result was comparable to that observed when fatty acid synthase was inhibited with cerulenin (FIG. 11B). Growth of the faa1Δ faa4Δ strain was restored under both conditionally lethal conditions by the introduction of expression plasmids containing either the FAA1 or FAA4 genes under the control of a galactose inducible promoter; as expected, growth was dependent upon inclusion of galactose in the culture media (FIG. 11). Thus, Faa1p and Faa4p can each activate saturated and unsaturated fatty acids imported from the environment to provide essential fatty acids required for growth.

These data did not distinguish whether these fatty acyl-CoA synthetases were required only for metabolic utilization of imported fatty acids or whether they were are also required for the transport process in a manner analogous to that which occurs in gram negative bacteria. In an effort to address whether there is a link between fatty acid import and activation in *S. cerevisiae*, studies were conducted to monitor the intracellular accumulation of the fluorescent fatty acid analogue C1-BODIPY-$C_{12}$ using CLSM. Wild-type cells accumulate exogenous C1-BODIPY-$C_{12}$ quickly (within 30 sec) by an essentially irreversible process suggesting this compound becomes metabolically trapped. See, Færgeman et al. (L997) *J. Biol. Chem.* 247: 8531–8538; DiRusso et al. (2000) *Eur. J. Biochem.* 267, 4422–4433. No efflux of C1-BODIPY-$C_{12}$ was noted using this experimental approach to monitor fatty acid import. See, DiRusso et al. (2000) *Eur. J. Biochem.* 267, 4422–4433. The accumulation of exogenous C1-BODIPY-$C_{12}$ was basically unchanged in the faa4Δ strain but considerably reduced in the faa1Δ strain (FIG. 12A). Deletion of both FAA1 and FAA4 reduced the accumulation of C1-BODIPY-$C_{12}$ further (FIG. 12A). These data are consistent with the notion that Faa1p plays a more prominent role in fatty acid import. Centromeric clones (pGALFAA1 and pGALFAA4) encoding these enzymes transformed into the faa1Δ faa4Δ strain led to a large increase in C1-BODIPY-$C_{12}$ accumulation when cells were grown in the presence of galactose to induce the expression of Faa1p or Faa4p (FIG. 12B). These findings attest to the importance of these two enzymes in the fatty acid import process. We hypothesize the irreversible nature of import is due to the metabolic trapping of C1-BODIPY-$C_{12}$, presumably as a CoA thioester as a consequence of either Faa1p or Faa4p.

Figure 12:
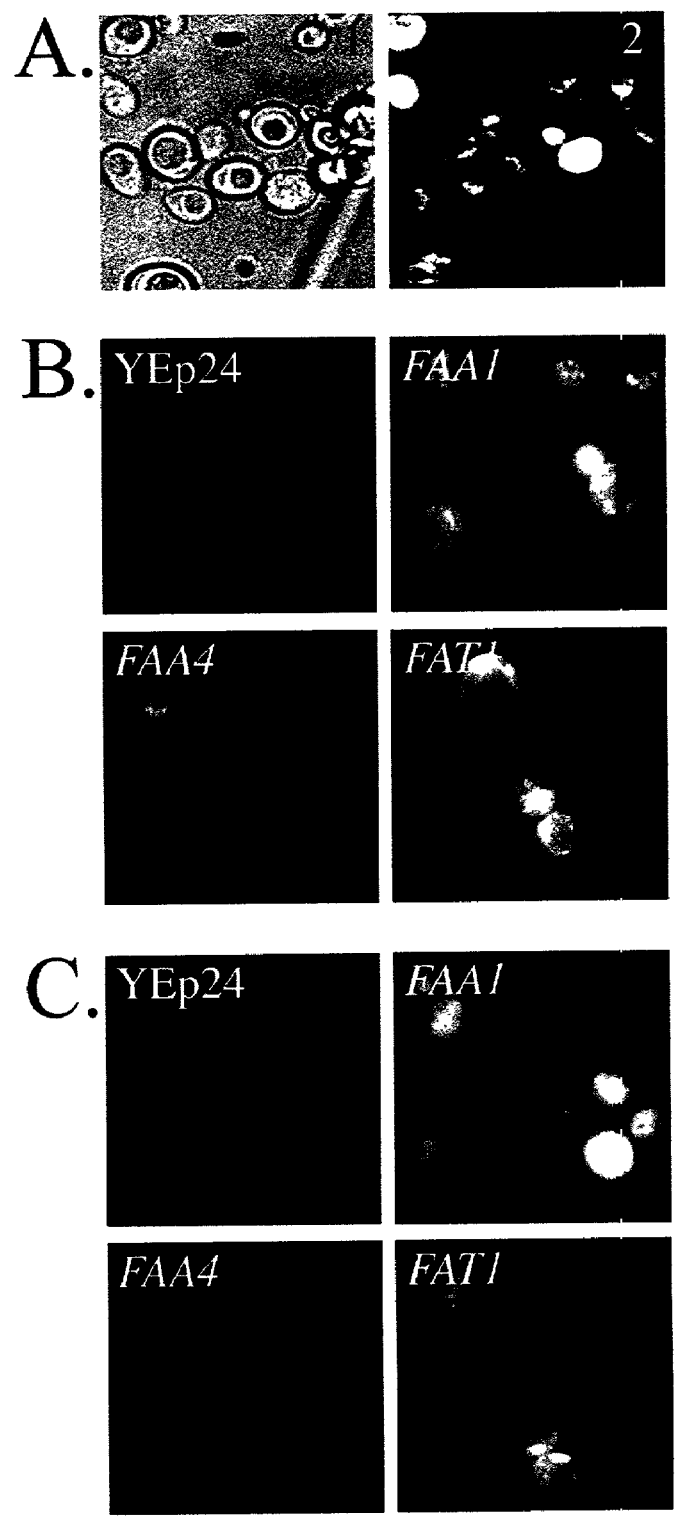

The results presented in FIG. 12 demonstrated the accumulation of the fluorescent fatty acid C1-BODIPY-$C_{12}$ was compromised in the faa1Δ faa4Δ strain and that expression of either FAA1 or FAA4 from a galactose inducible promoter on a plasmid following transformation in essence restored the wild type activity. These data lend support to the hypothesis that fatty acid import is indeed linked to activation in yeast. In an effort to quantify these results at the level of fatty acid import, we used the filtration method (see, Færgeman et al. (1997) *J. Biol. Chem.* 247: 8531–8538; DiRusso et al. (2000) *Eur. J. Biochem.* 267, 4422–4433) to monitor the import of [$^3$H] oleate in wild type and fatty acyl-CoA deficient strains as detailed in Experimental Methods (Table 2).

TABLE 2

Long-chain fatty acid transport profiles in wild type and acyl-CoA synthetase-deficient strains of *Saccharomyces cerevisiae* determined using the filtration assay

| | Oleate Uptake (pmol/min/1 × 10$^8$ cells)(±SE)[1] Oleate:BSA[2] | | |
|---|---|---|---|
| | 0.5 | 1.0 | 2.0 |
| Strain | | | |
| Wild-Type | 42.1 (10.6) | 96.5 (20.9) | 273.1 (30.3) |
| faa1Δ | 18.7 (8.1) | 47.6 (16.9) | 98.8 (21.5)[3] |
| faa4Δ | 30.5 (6.3) | 142.3 (30.1)[3] | 306.2 (33.0) |

[1]SE - standard error of the mean, n = 2
[2]Fatty acid free BSA is held constant at 173 μM and [$^3$H] oleate concentration varied to give the designated ratios giving 60 nM, 125 nM or 400 nM free fatty acid.
[3]p = 0.1; data analyzed using ANOVA; significance is relative to the wild-type strain As with the experimental approach detailed above using C1-BODIPY-$C_{12}$, there was no measurable efflux of the labeled fatty acid following transport. See, Færgeman et al. (1997) *J. Biol. Chem.* 247: 8531–8538; DiRusso et al. (2000) *Eur. J. Biochem.* 267, 4422–4433. These results revealed that a deletion of FAA1 decreased oleate import nearly two-fold while a deletion of FAA4 basically had no effect. While the reduction in import in the faa1Δ strain was the trend at oleate:BSA ratios of 0.5 and 1.0 (p=0.1), the reduction in import noted at the Oo higher concentration of oleate was significant (oleate:BSA=2.0; p<0.1). The results acquired for the wild-type, faa1Δ and faa4Δ strains using the filtration method essentially mirrored those obtained using the C1-BODIPY-$C_{12}$. The unexpected result came from measuring the transport of [$^3$H] oleate using the filtration method on the faa1Δ faa4Δ strain, which had apparent levels of fatty acid import that were nearly ten-fold higher than wild type. The fatty acid import measurements in the faa1Δ faa4Δ strain were complicated by a flocculent phenotype, suggesting the cell surface was altered in some manner, which resulted in cells becoming clumped during growth in liquid media. This flocculent phenotype was not observed in the faa4Δ strain. The high density of cells required for the filtration assay appears to exacerbate this problem and resulted in what we interpret as high levels of non-specific fatty acid binding. We predicted the faa1Δ faa4Δ strain would have fatty acid import values comparable to or lower than the fat1Δ strain, which is defective in the import of [$^3$H] oleate. See, DiRusso et al. (2000) *Eur. J. Biochem.* 267, 4422–4433. The levels of [$^3$H] oleate import in the fat1Δ strain, by comparison to the wild-type strain, were reduced nearly five-fold at all three fatty acid concentrations tested. See, DiRusso et al. (2000) *Eur. J. Biochem.* 267, 4422–4433. The most informative observation derived from these data using the filtration method was the depressed levels of oleate transport in the faa1Δ strain. The phenotype associated with this strain on the fatty acid, cerulenin-containing plates and under anaerobic conditions suggests Faa1p plays a more predominant role in activating exogenous long-chain fatty acids, when compared to Faa4p. The fatty acid import data obtained using both C1-BODIPY-$C_{12}$ and [$^3$H] oleate seems to corroborate these findings.

In vivo Activation of Imported Fatty Acids and Maintenance of Endogenous Acyl-CoA Pools Yeast strains harboring deletions in both FAA1 and FAA4 had levels of fluorescent fatty acid accumulation appreciably reduced when compared to the isogenic wild type parent attesting to the functional role of fatty acyl-CoA synthetase in this process. In order to investigate the linkage between import, activation and subsequent trafficking, we measured intracellular oleoyl-CoA pools in wild-type, faa1Δ, faa4Δ and faa1Δ faa4Δ strains following the addition of oleate (final concentration—100 μM) to actively growing cells cultured in YNBD media. We chose to use 100 μM oleate for these experiments as our phenotypic data demonstrated the restrictive concentrations for fatty acid supplementation when fatty acid synthetase is inhibited was between 50 and 75 μM oleate. Aliquots of cells were removed at various time points (t=10, 30, 60 and 120 min) after oleate addition and oleoyl-CoA levels quantified as detailed in Experimental Methods. As a baseline, endogenous oleoyl-CoA levels were defined prior to the addition of exogenous oleate. Within 10 min after the addition of $C_{18:1}$, oleoyl-CoA levels increased nearly six-fold in wild-type cells (FIG. 13). By comparison, the oleoyl-CoA levels for the faa1Δ, faa4Δ, and faa1Δ faa4Δ strains were either reduced or not responsive to added oleate when compared to the wild type strain. For the faa4Δ cells the measured oleoyl-CoA levels derived from exogenous oleate were between 45–55% of wild type. Deletion of FAA1, in contrast, resulted in a severe reduction of oleoyl-CoA at all time points evaluated (<10% wild-type levels). There was not a significant difference in oleoyl-CoA levels between cells from the strain deleted for FAA1 alone compared to those with deletions in both FAA1 and FAA4 or all four FAA genes (FIG. 13). It should be noted that these are not kinetic measurements per se, but rather measurements, which established the linkage between exogenous oleate and intracellular oleoyl CoA pools. These observations confirmed that Faa1p is the principal acyl-CoA synthetase responsible for the activation of exogenous fatty acids. Additional significant findings from these experiments came from the base-line measurements of endogenous acyl CoA pools in the faa1Δ, faa4Δ and faa1Δ faa4Δ strains.

Strains harboring deletions in FAA1 and/or FAA4 had endogenous oleoyl-CoA pools, which were only ~20% those measured for the wild type strain. This observation led us to measure endogenous levels of other long chain acyl-CoA species i a cells grown in the absence of exogenous fatty acids (Table 3). Total long chain acyl-CoA levels were reduced to 74% and 39% wild-type levels in the faa1Δ and faa1Δ faa4Δ strains, respectively. While the total long-chain acyl -CoA profile in the faa4Δ strain was equivalent to the wild type strain, there were notable differences, particularly in C16:0-CoA levels, which were elevated two-fold over the wild type. The reduction in the acyl CoA pools in the faa1Δ, faa4Δ and faa1Δ faa4Δ strains was particularly pronounced for the unsaturated acyl-CoA esters ($C_{16:1}$ and $C_{18:1}$). The levels of saturated long-chain fatty acyl-CoA esters ($C_{14:0}$ and $C_{16:0}$) were in creased in the faa4Δ strain by approximately 33%, which was due to the spike in C16:0 CoA levels as noted above. Deletion of both the FAA1 and FAA4 genes reduced the total acyl-CoA ester levels to 39% wild type levels. In this strain the levels of saturated and unsaturated long-chain acyl CoAs were 53% and 19% wild type respectively indicating a cooperative role between Faa1p and Faa4 in the maintenance of intracellular acyl-CoA pools.

TABLE 3

Endogenous acyl-CoA profiles in wild type and fatty acyl-CoA synthetase-deficient strains

| | Acyl-CoA Profiles (±SE)[1] nmol acyl-CoA/2 × 10$^9$ cells Strain | | | |
|---|---|---|---|---|
| Acyl-CoA | Wild-Type | faa1Δ | faa4Δ | faa1Δfaa4Δ |
| C14:0 | 0.14 (0.01) | 0.18 (0.01) | 0.35 (0.01) | 0.10 (0.01) |
| C16:0 | 0.75 (0.02) | 0.78 (0.03) | 1.64 (0.01) | 0.42 (0.05) |
| C16:1 | 1.11 (0.12) | 0.69 (0.08) | 0.38 (0.02) | 0.23 (0.02) |
| C18:0 | 0.87 (0.01) | 0.65 (0.01) | 0.81 (0.02) | 0.45 (0.02) |
| C18:1 | 0.40 (0.02) | 0.11 (0.04) | 0.1 (0.01) | 0.06 (0.01) |
| Total | 3.27 (0.05) | 2.41 (0.02) | 3.28 (0.03) | 1.26 (0.03) |
| SFA[2] | 1.76 | 1.61 | 2.80 | 0.97 |
| UFA[2] | 1.51 | 0.80 | 0.48 | 0.29 |

[1]SE - standard error of the mean, n = 2
[2]SFA - total saturated acyl-CoA pool; UFA - total unsaturated acyl-CoA pool The data presented above documented unique biochemical phenotypes of the faa1Δ and faa4Δ strains indicating that Faa1p and Faa4p are not completely functionally redundant, and indeed further support the hypothesis that Faa1p is the predominant acyl-CoA synthetase involved in the fatty acid import and activation processes. Previously, acyl-CoA synthetase activities were measured in wild type and faa1Δ faa4Δ strains using saturated fatty acid substrates. See, Knoll et al. (1995) *J. Biol. Chem.* 270: 10861–10867. It was expected that the severe reduction of oleoyl-CoA found for the faa1Δ strain by comparison with the faa4Δ strain should be reflected in reduced enzyme activity. Therefore we measured oleoyl-CoA synthetase activities in total cellular extracts of each strain (Table 4). We found the oleoyl-CoA synthetase profiles measured in these experiments mirrored the data obtained on the oleoyl-CoA levels in the wild type and different mutant strains. Of particular note was the finding that deletion of FAA1 resulted in oleoyl-CoA synthetase levels that were only 7% those measured in the wild-type cells. By contrast, the faa4Δ strain had oleoyl-CoA synthetase levels that were nearly three-fold higher than the faa1Δ strain, but only 22% of wild type levels. Deletion of both FAA1 and FAA4 or all four FAA genes reduced acyl-CoA synthetase levels further (to 5% wild type), but did not eliminate all activity.

TABLE 4

Fatty acyl-CoA synthetase activities in cell extracts using oleate ($C_{18:1}$) as the fatty acid substrate in wild type and strains defective in one or more fatty acyl-CoA synthetase

| Oleoyl-CoA Synthetase Activity | (pmol/min/mg protein (±SE))[1] |
|---|---|
| Wild-Type | 3,888.96 (382.19) |
| faa1Δ | 258.70 (36.36) |
| faa4Δ | 866.58 (210.55) |
| faa1Δfaa4Δ | 190.00 (49.67) |
| faa1Δfaa2Δfaa3Δfaa4Δ | 180.45 (27.25) |

[1]SE - standard error of the mean, n = 4

The reductions in the intracellular acyl-CoA pools were particularly notable in the faa1Δ and faa1Δ faa4Δ strains. To address whether these reduced acyl-CoA levels also resulted in altering the cellular fatty acid levels, we identified and quantified total cellular fatty acids and showed that the fatty acid profiles in the faa1Δ and faa1Δ faa4Δ strains were essentially unchanged compared to wild type (Table 5). This is in contrast to the fatty acid profiles of a fat1Δ strain (defective in fatty acid import and lignoceryl CoA synthetase activity) where marked differences in the very long-chain fatty acid pools relative to the wild type are found. These data indicate de novo fatty acid synthesis provides sufficient long chain saturated and unsaturated fatty acyl-CoAs to maintain normal levels required for higher lipid synthesis and other process essential to cell growth. Therefore, while deficiency in the long-chain fatty acid activating enzymes eliminates incorporation of exogenous fatty acids into higher lipids, there was no detectable effect on fatty acid incorporation from endogenous pools into higher lipids under the growth conditions used for these studies.

TABLE 5

Total fatty acid profiles in wild type and fatty acyl-CoA synthetase-deficient strains

| | mole % (±SE)[1] | | | |
|---|---|---|---|---|
| Fatty Acid | Wild-Type | faa1Δ | faa4Δ | faa1Δfaa4Δ |
| C10:0 | 0.667 (0.088) | 0.400 (0.100) | 0.700 (0.100) | 0.400 (0.200) |
| C12:0 | 1.633 (0.120) | 1.600 (0.200) | 2.050 (0.250) | 1.450 (0.550) |
| C14:0 | 3.033 (0.176) | 3.300 (0.600) | 4.350 (0.350) | 3.750 (1.050) |
| C16:0 | 17.667 (0.689) | 20.500 (1.700) | 17.150 (0.050) | 19.750 (0.750) |
| C16:1 | 43.767 (0.521) | 39.800 (2.100) | 46.150 (0.550) | 38.150 (0.550) |
| C18:0 | 4.467 (0.133) | 6.400 (0.500) | 4.050 (0.350) | 6.050 (0.350) |
| C18:1 | 25.067 (0.481) | 26.300 (1.300) | 23.350 (0.150) | 28.550 (1.850) |
| C20:0 | 0.200 (0.000) | 0.200 (0.000) | 0.200 (0.000) | 0.150 (0.050) |
| C22:0 | 0.167 (0.033) | 0.200 (0.000) | 0.150 (0.050) | 0.150 (0.050) |
| C24:0 | 0.300 (0.000) | 0.200 (0.000) | 0.200 (0.000) | 0.150 (0.050) |
| C26:0 | 1.467 (088) | 1.400 (0.100) | 0.850 (0.050) | 0.850 (0.050) |

[1]SE - standard error of the mean, n = 3

Intracellular Trafficking of Exogenously Derived Acyl-CoA

The data presented above demonstrated fatty acid import and activation are severely compromised in the faa1Δ faa4Δ strain, fully supporting our hypothesis that one or both enzymes function as components of a fatty acid import system. In addition, the endogenous acyl-CoA pools were markedly reduced in the faa1Δ faa4Δ strain supporting the notion that these enzymes are also involved in endogenous acyl-CoA metabolism. To further investigate the linkage between import, activation and trafficking, we defined (1) the levels of β-oxidation of exogenous fatty acids (to monitor utilization) and (2) differential expression of POX1 and FAA2 (encoding the peroxisomal genes acyl-CoA oxidase and medium-chain acyl-CoA synthetase respectively; to monitor intracellular signaling) in response to exogenous fatty acids.

In order to assess the role of fatty acid activating enzymes on the β-oxidation pathway, we analyzed the ability of yeast cells containing deletions in the FAA genes to degrade exogenously supplied oleate in vivo. For these studies, cells were cultured under conditions required for the induction of peroxisomes as detailed in Experimental Methods. β-oxidation levels of exogenous oleate in strains containing deletions of FAA1 or FAA4 were reduced to 70% and 85% wild-type levels, respectively. Deletion of both genes reduced β-oxidation levels to 25% wild type (FIG. 14). In this case, each activating enzyme Faa1p and Faa4p appears to contribute to the acyl-CoA substrate pool. Deletion of both genes had a more substantial effect on the overall rate of β-oxidation than either enzyme alone. This is in striking contrast to the dominant role of Faa1p over Faa4p noted above. We suggest this may be due to the differences in growth conditions used for each assay. For the measurement of acyl-CoA and fatty acid pools, cells were incubated 0–120 min in minimal media with glucose as the carbon source and limiting concentrations (μM) of oleate whereas for β-oxidation assays cells were grown overnight in YP medium containing glycerol and 4mM oleate prior to assaying in a reaction mixture containing 10 μM [$^{14}$C] oleate.

As a second measure of the roles of Faa1p and Faa4p in intracellular fatty acid trafficking, we monitored the expression of genes activated by fatty acids (POX1 and FAA2) using Northern analyses of RNA prepared from the wild type strain or strains defective in the fatty acid activating genes. For comparison and as a control, we monitored the repression of OLE1 mRNA (encoding the $\Delta^9$ acyl-CoA desaturase). It has been. previously demonstrated that oleate-mediated repression of OLE1 requires FAA1 or FAA4. See, Choi et al. (1996) J. Biol. Chem. 271: 3581–3589. As expected OLE1 expression was high in wild-type cells cultured in glucose or in glycerol. The addition of oleic acid essentially eliminated OLE1 expression and repression of OLE1 was dependent on Faa1p or Faa4p. In the case of POX1 and FAA2, there was also a dependence of Faa1p or Faa4p in linking increased expression to exogenous fatty acid. This is the first work that demonstrates either Faa1p or Faa4p must be active to induce the expression of POX1 and FAA2. Unlike OLE1, however, the expression of patterns of POX1 and FAA2 were more complex. First both FAA2 and POX1 were subject to catabolite repression mediated by glucose. Second, the expression of both genes was detectable when cells were cultured in media containing glycerol (non-catabolite repressing conditions). Third, in wild type, faa1Δ and faa4Δ strains, the expression of both FAA2 and POX1 was high when cells were cultured in oleate-containing medium (FIG. 15). Deletion of both FAA1 and FAA4 eliminated the increased expression of both genes in response to oleate in the culture media. We noted the expression of FAA2 and POX1 in the faa1Δ faa4Δ strain was elevated when cells were grown in media containing glycerol when compared to the wild type, faa1Δ and faa4Δ strains. These results are similar to those observed in strains carrying a deletion in the gene encoding the transcription factor Pip2p. See, Karpichev & Small (998) *Mol. Cell. Biol.* 18: 6560–6570.

On the basis of these data, we conclude the fatty acyl CoA synthetases Faa1p and Faa4p function as components of a fatty acid transport and activation system linking import and trafficking of exogenous fatty acids to sites of utilization (β-oxidation) and intracellular signaling (differential expression of genes involved in fatty acid metabolism).

Fatty acid import in yeast, as in bacteria and mammals, is a complex multi-component process. In the well-characterized *E. coli* system, fatty acid transport, activation, metabolic utilization and gene regulation are tightly coupled processes. Some mammalian systems are believed to operate by similar mechanisms. For example, in adipocytes, FATP (the mammalian orthologue of Fat1p) has been linked to fatty acyl-CoA synthetase both by functional assays, expression patterns and cellular localization. As in yeast, mammalian ACBP is believed to play a significant role in intracellular transport and trafficking of acyl-CoAs. The yeast system offers a powerful tool with which to investigate other components in fatty acid trafficking due to ability to grow on fatty acids as a sole carbon and energy source and to natural, conditional auxotrophy for unsaturated fatty acids when cells grow anaerobically.

Equivalents

Those skilled in the art will recognize, or be able to ascertain using no more than routine experimentation, numerous equivalents to the specific procedures described herein. Such equivalents are considered to be within the scope of the present invention and are covered by the following claims. Various substitutions, alterations, and modifications may be made to the invention without departing from the spirit and scope of the invention as defined by the claims. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the present invention and embodiments thereof.

What is claimed is:

1. A method for identifying modulators of fatty acid uptake, comprising:
   a) supplying a fatty acid to a test system comprising yeast test cells and yeast control cells wherein the genotype of the test cells and control cells is fat1Δ faa1Δ, and wherein said test cells and control cells have been transfected with a vector expressing a mammalian fatty acid transport mediator protein ("TTMp");
   b) contacting a putative modulator with the test cells, but not the control cells;
   c) measuring accumulation of the fatty acid in the test cells and control cells; and
   d) comparing accumulation of the fatty acid in the test cells with accumulation of the fatty acid in the control cells, wherein a lesser quantity of fatty acid accumulated in the test cells compared to the control cells indicates that the putative modulator is an inhibitor of fatty acid uptake, and wherein a greater quantity of fatty acid accumulated in the test cells compared to the control cells indicates that the putative modulator is an enhancer of fatty acid uptake.

2. The method of claim 1, wherein said fatty acid is detectably labeled.

3. The method of claim 2, wherein said detectable label is a fluorescent or radioactive label.

4. The method of claim 1, wherein said mammalian TTMp is derived from either a mouse or a human.

5. The method of claim 1, wherein said TTMp is derived from the same mammalian species as the putative modulator of fatty acid uptake.

6. The method of claim 1, wherein said TTMp is FATP or isoforms thereof.

7. A method for identifying modulators of fatty acid uptake, comprising:
   a) supplying a fatty acid to a test system comprising yeast test cells and yeast control cells wherein the genotype of the test cells and control cells is fat1Δ faa4Δ, and wherein said test cells and control cells have been transfected with a vector expressing a mammalian fatty acid transport mediator protein ("TTMp");
   b) contacting a putative modulator with the test cells, but not the control cells;
   c) measuring accumulation of the fatty acid in the test cells and control cells; and
   d) comparing accumulation of the fatty acid in the test cells with accumulation of the fatty acid in the control cells, wherein a lesser quantity of fatty acid accumulated in the test cells compared to the control cells indicates that the putative modulator is an inhibitor of fatty acid uptake, and wherein a greater quantity of fatty acid accumulated in the test cells compared to the control cells indicates that the putative modulator is an enhancer of fatty acid uptake.

8. The method of claim 7, wherein said fatty acid is detectably labeled.

9. The method of claim 8, wherein said detectable label is a fluorescent or radioactive label.

10. The method of claim 7, wherein said mammalian TTMp is derived from either a mouse or a human.

11. The method of claim 7, wherein said TTMp is derived from the same mammalian species as the putative modulator of fatty acid uptake.

12. The method of claim 7, wherein said TTMp is FATP or isoforms thereof.

13. A method for identifying modulators of fatty acid uptake, comprising:
   a) supplying a fatty acid to a test system comprising yeast test cells and yeast control cells wherein the genotype of the test cells and control cells is fat1Δ faa1Δ faa4Δ, and wherein said test cells and control cells have been transfected with a vector expressing a mammalian fatty acid transport mediator protein ("TTMp");
   b) contacting a putative modulator with the test cells, but not the control cells;
   c) measuring accumulation of the fatty acid in the test cells and control cells; and
   d) comparing accumulation of the fatty acid in the test cells with accumulation of the fatty acid in the control cells, wherein a lesser quantity of fatty acid accumulated in the test cells compared to the control cells indicates that the putative modulator is an inhibitor of fatty acid uptake, and wherein a greater quantity of fatty acid accumulated in the test cells compared to the control cells indicates that the putative modulator is an enhancer of fatty acid uptake.

14. The method of claim 13, wherein said fatty acid is detectably labeled.

15. The method of claim 14, wherein said detectable label is a fluorescent or radioactive label.

16. The method of claim 13, wherein said mammalian TTMp is derived from either a mouse or a human.

17. The method of claim 13, wherein said TTMp is derived from the same mammalian species as the putative modulator of fatty acid uptake.

18. The method of claim 13, wherein said TTMp is FATP or isoforms thereof.

* * * * *

UNITED STATES PATENT AND TRADEMARK OFFICE
CERTIFICATE OF CORRECTION

PATENT NO. : 7,070,944 B2  Page 1 of 1
APPLICATION NO. : 10/099350
DATED : July 4, 2006
INVENTOR(S) : Black et al.

It is certified that error appears in the above-identified patent and that said Letters Patent is hereby corrected as shown below:

On the Title Page
Item (73), the Assignee should be: "Albany Medical College" (US)
Albany, NY (US)

Signed and Sealed this

Seventeenth Day of February, 2009

JOHN DOLL
*Acting Director of the United States Patent and Trademark Office*

```
                          SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:FAT1 forward
      primer

<400> SEQUENCE: 1
caggttcttg cttgtctttg g                                             21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:FAT1 reverse
      primer

<400> SEQUENCE: 2
ggagtgagaa ggatgctcta a                                             21

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:FAT1
      oligonucleotide containing a BamH1 site at +1 of
      translation of FAT1

<400> SEQUENCE: 3
cgcggatcca tgtctcccat acaggtt                                       27

<210> SEQ ID NO 4
<211> LENGTH: 34
<212> TYPE: DNA
<213> ORGANISM: Artificial Sequence
```

-continued

```
<220> FEATURE:
<223> OTHER INFORMATION: Description of Artificial Sequence:FAT1
      oligonucleotide containing an XhoI site at the
      termination of the FAT1 coding sequence

<400> SEQUENCE: 4
aagctcgagt gataatttaa ttgtttgtgc atcg                                    34
```